US010905476B2

(12) United States Patent
Lopez et al.

(10) Patent No.: US 10,905,476 B2
(45) Date of Patent: Feb. 2, 2021

(54) VARIABLE ANGLE BONE PLATE

(71) Applicant: DePuy Synthes Products, Inc., Raynham, MA (US)

(72) Inventors: Erasmo A. Lopez, West Chester, PA (US); Kristina Snyder, Exton, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 812 days.

(21) Appl. No.: 15/260,919

(22) Filed: Sep. 9, 2016

(65) Prior Publication Data

US 2018/0064476 A1 Mar. 8, 2018

Related U.S. Application Data

(60) Provisional application No. 62/385,107, filed on Sep. 8, 2016.

(51) Int. Cl.
*A61B 17/80* (2006.01)
*A61B 17/86* (2006.01)

(52) U.S. Cl.
CPC ...... *A61B 17/8014* (2013.01); *A61B 17/8057* (2013.01); *A61B 17/8061* (2013.01); *A61B 17/8605* (2013.01)

(58) Field of Classification Search
CPC .............. A61B 17/864; A61B 17/8014; A61B 17/8052; A61B 17/8057; A61B 17/86
See application file for complete search history.

(56) References Cited

U.S. PATENT DOCUMENTS

| 327,296 A | 9/1885 | Mcginnis |
| 1,105,105 A | 7/1914 | Sherman |
| 1,203,546 A | 10/1916 | Parsons |
| 2,228,584 A | 1/1941 | Place |
| 2,352,297 A | 6/1944 | Wales |
| 2,414,882 A | 1/1947 | Longfellow |
| 2,443,363 A | 6/1948 | Kenneth et al. |
| 2,477,430 A | 7/1949 | Swanstrom |
| 2,496,126 A | 1/1950 | Haboush |

(Continued)

FOREIGN PATENT DOCUMENTS

| CA | 1112803 A | 11/1981 |
| CA | 2047521 A1 | 1/1992 |

(Continued)

OTHER PUBLICATIONS

U.S. Appl. No. 15/940,761, Locking Structures for Affixing Bone Anchors to a Bone Plate, and Related Systems and Methods, filed Mar. 29, 2018.

(Continued)

*Primary Examiner* — Anu Ramana
(74) *Attorney, Agent, or Firm* — BakerHostetler

(57) ABSTRACT

A bone plate having at least one variable angle locking hole is described. The variable angle locking hole allows a bone anchor having a threaded head to be driven into underlying bone while oriented at an angle with respect to a central hole axis of the hole that is within a range of angles at which the head is configured to threadedly mate with the at least one thread of the bone plate. Accordingly, the bone anchor can be driven into the underlying bone until the threaded head threadedly purchases with the bone plate inside the variable angle locking hole.

10 Claims, 6 Drawing Sheets

(56) References Cited

U.S. PATENT DOCUMENTS

| | | |
|---|---|---|
| 2,526,959 A | 10/1950 | Lorenzo |
| 2,612,159 A | 9/1952 | Collison |
| 2,627,855 A | 2/1953 | Price |
| 2,699,774 A | 1/1955 | Livingston |
| 2,772,676 A | 12/1956 | Pohl |
| 2,801,631 A | 8/1957 | Charnley |
| 2,846,701 A | 8/1958 | Bedford, Jr. |
| 2,874,691 A | 2/1959 | Mason |
| 3,025,853 A | 3/1962 | Mason |
| 3,229,743 A | 1/1966 | Derby |
| 3,263,949 A | 8/1966 | Conrad |
| 3,314,326 A | 4/1967 | Bedford, Jr. |
| 3,364,807 A | 1/1968 | Holton |
| 3,374,786 A | 3/1968 | Callender, Jr. |
| 3,388,732 A | 6/1968 | Holton |
| 3,463,148 A | 8/1969 | Treace |
| 3,489,143 A | 1/1970 | Halloran |
| 3,534,731 A | 10/1970 | Muller |
| 3,551,389 A | 12/1970 | Prince, Jr. |
| 3,552,389 A | 1/1971 | Allgower et al. |
| 3,561,437 A | 2/1971 | Orlich |
| 3,577,601 A | 5/1971 | Mariani et al. |
| 3,630,261 A | 12/1971 | Gley |
| 3,668,972 A | 6/1972 | Russenberger |
| 3,688,972 A | 9/1972 | Mahon |
| 3,695,259 A | 10/1972 | Yost |
| 3,695,618 A | 10/1972 | Woolley et al. |
| 3,716,050 A | 2/1973 | Johnston |
| 3,741,205 A | 6/1973 | Harris |
| 3,744,488 A | 7/1973 | Cox |
| 3,779,240 A | 12/1973 | Kondo |
| 3,782,374 A | 1/1974 | Fischer |
| 3,824,995 A | 7/1974 | Getscher et al. |
| 3,842,825 A | 10/1974 | Wagner |
| 3,877,339 A | 4/1975 | Muenchinger |
| RE28,841 E | 6/1976 | Allgower et al. |
| 3,967,049 A | 6/1976 | Brandt |
| 3,996,834 A | 12/1976 | Reynolds |
| 3,996,931 A | 12/1976 | Callender, Jr. |
| 4,009,712 A | 3/1977 | Burstein et al. |
| 4,029,091 A | 6/1977 | Kraus |
| 4,040,129 A | 8/1977 | Steinemann et al. |
| 4,095,591 A | 6/1978 | Graham et al. |
| 4,120,298 A | 10/1978 | Fixel |
| 4,172,452 A | 10/1979 | Forte et al. |
| 4,175,555 A | 11/1979 | Herbert |
| 4,219,015 A | 8/1980 | Steinemann |
| 4,236,512 A | 12/1980 | Aginsky |
| 4,263,904 A | 4/1981 | Judet |
| 4,269,180 A | 5/1981 | Dall et al. |
| 4,304,039 A | 12/1981 | Asmus |
| 4,338,926 A | 7/1982 | Kummer et al. |
| 4,355,198 A | 10/1982 | Gartland, Jr. |
| 4,379,451 A | 4/1983 | Getscher |
| 4,388,921 A | 6/1983 | Sutter et al. |
| 4,408,601 A * | 10/1983 | Wenk ............... A61B 17/8014 606/282 |
| 4,429,690 A | 2/1984 | Angelino-Pievani |
| 4,438,762 A | 3/1984 | Kyle |
| 4,454,876 A | 6/1984 | Mears |
| RE31,628 E | 7/1984 | Allgower et al. |
| 4,484,570 A | 11/1984 | Sutter et al. |
| 4,484,750 A | 11/1984 | Scruggs |
| 4,488,543 A | 12/1984 | Tornier |
| 4,491,317 A | 1/1985 | Bansal |
| 4,493,317 A | 1/1985 | Klaue |
| 4,494,535 A | 1/1985 | Haig |
| 4,513,744 A | 4/1985 | Klaue |
| 4,537,185 A | 8/1985 | Stednitz |
| 4,565,193 A | 1/1986 | Streli |
| 4,580,225 A | 4/1986 | Thompson |
| 4,612,920 A | 9/1986 | Lower |
| 4,612,923 A | 9/1986 | Kronenthal |
| 4,616,638 A | 10/1986 | Griggs |
| 4,617,922 A | 10/1986 | Griggs |
| 4,621,629 A | 11/1986 | Koeneman |
| 4,628,923 A | 12/1986 | Medoff |
| 4,629,455 A | 12/1986 | Kanno |
| 4,630,985 A | 12/1986 | Simons |
| 4,651,724 A | 3/1987 | Berentey et al. |
| 4,657,001 A | 4/1987 | Fixel |
| 4,683,878 A | 8/1987 | Carter |
| 4,717,613 A | 1/1988 | Ottaviano |
| 4,747,613 A | 5/1988 | Brichoud et al. |
| 4,776,329 A | 10/1988 | Treharne |
| 4,776,330 A | 10/1988 | Chapman et al. |
| 4,781,183 A | 11/1988 | Casey et al. |
| 4,791,918 A | 12/1988 | Von Hasselbach |
| 4,794,918 A | 1/1989 | Wolter |
| 4,795,473 A | 1/1989 | Grimes |
| 4,800,874 A | 1/1989 | David et al. |
| 4,838,252 A | 6/1989 | Klaue |
| 4,848,328 A | 7/1989 | Laboureau et al. |
| 4,858,601 A | 8/1989 | Glisson |
| 4,867,144 A | 9/1989 | Karas et al. |
| 4,903,691 A | 2/1990 | Heinl |
| 4,905,680 A | 3/1990 | Tunc |
| 4,927,421 A | 5/1990 | McGuire |
| 4,955,886 A | 9/1990 | Pawluk |
| 4,957,496 A | 9/1990 | Schmidt |
| 4,957,497 A | 9/1990 | Behrens |
| 4,964,403 A | 10/1990 | Karas et al. |
| 4,966,599 A | 10/1990 | Pollock |
| 4,973,332 A | 11/1990 | Kummer |
| 4,973,333 A | 11/1990 | Treharne |
| 4,988,350 A | 1/1991 | Herzberg |
| 5,002,544 A | 3/1991 | Klaue et al. |
| 5,006,120 A | 4/1991 | Carter |
| 5,013,313 A | 5/1991 | Surer |
| 5,013,315 A | 5/1991 | Barrows |
| 5,015,248 A | 5/1991 | Burstein et al. |
| 5,027,904 A | 7/1991 | Bardine |
| 5,039,265 A | 8/1991 | Rath et al. |
| 5,041,113 A | 8/1991 | Harms |
| 5,041,114 A | 8/1991 | Chapman et al. |
| 5,041,116 A | 8/1991 | Wilson |
| 5,053,036 A | 10/1991 | Perren et al. |
| 5,085,660 A | 2/1992 | Lin |
| 5,087,260 A | 2/1992 | Fixel |
| 5,108,399 A | 4/1992 | Eitenmuller et al. |
| 5,108,449 A | 4/1992 | Gray |
| 5,116,336 A | 5/1992 | Frigg |
| 5,127,914 A | 7/1992 | Calderale et al. |
| 5,129,901 A | 7/1992 | Decoste |
| 5,139,497 A | 8/1992 | Tilghman et al. |
| 5,147,361 A | 9/1992 | Ojima et al. |
| 5,147,363 A | 9/1992 | Harle |
| 5,151,103 A | 9/1992 | Tepic et al. |
| 5,152,794 A | 10/1992 | Davidson |
| 5,190,544 A | 3/1993 | Chapman et al. |
| 5,197,966 A | 3/1993 | Sommerkamp |
| 5,201,733 A | 4/1993 | Etheredge, III |
| 5,261,910 A | 11/1993 | Warden et al. |
| 5,269,784 A | 12/1993 | Mast |
| 5,275,601 A | 1/1994 | Gogolewski et al. |
| 5,290,281 A | 3/1994 | Tschakaloff |
| 5,300,074 A | 4/1994 | Frigg |
| 5,304,180 A | 4/1994 | Slocum |
| 5,306,275 A | 4/1994 | Bryan |
| 5,324,290 A | 6/1994 | Zdeblick et al. |
| 5,324,292 A | 6/1994 | Meyers |
| 5,336,224 A | 8/1994 | Selman |
| 5,356,410 A | 10/1994 | Pennig |
| 5,360,429 A | 11/1994 | Jeanson et al. |
| 5,360,448 A | 11/1994 | Thramann |
| 5,364,398 A | 11/1994 | Chapman et al. |
| 5,364,399 A | 11/1994 | Lowery et al. |
| 5,372,598 A | 12/1994 | Luhr et al. |
| 5,376,126 A | 12/1994 | Lin |
| 5,395,372 A | 3/1995 | Holt et al. |
| 5,403,136 A | 4/1995 | Mathys |
| 5,413,577 A | 5/1995 | Pollock |
| 5,429,641 A | 7/1995 | Gotfried |
| 5,433,719 A | 7/1995 | Pennig |

(56) References Cited

U.S. PATENT DOCUMENTS

| | | |
|---|---|---|
| 5,458,654 A | 10/1995 | Tepic |
| 5,462,547 A | 10/1995 | Weigum |
| 5,484,439 A | 1/1996 | Olson et al. |
| 5,514,138 A | 5/1996 | McCarthy |
| 5,520,690 A | 5/1996 | Errico et al. |
| 5,522,902 A | 6/1996 | Yuan et al. |
| 5,531,746 A | 7/1996 | Errico et al. |
| 5,534,032 A | 7/1996 | Hodorek |
| 5,558,674 A | 9/1996 | Heggeness et al. |
| 5,569,248 A | 10/1996 | Mathews |
| 5,571,109 A | 11/1996 | Bertagnoli |
| 5,571,198 A | 11/1996 | Drucker |
| 5,586,985 A | 12/1996 | Putnam et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,427 A | 3/1997 | Tschakaloff |
| 5,607,428 A | 3/1997 | Lin |
| 5,620,445 A | 4/1997 | Brosnahan et al. |
| 5,647,872 A | 7/1997 | Gilbert et al. |
| 5,655,089 A | 8/1997 | Bucci |
| 5,658,339 A | 8/1997 | Tronzo et al. |
| 5,662,655 A | 9/1997 | Laboureau et al. |
| 5,674,222 A | 10/1997 | Berger et al. |
| 5,676,667 A | 10/1997 | Hausman |
| 5,681,311 A | 10/1997 | Foley et al. |
| D385,963 S | 11/1997 | Hansson |
| 5,690,633 A | 11/1997 | Taylor et al. |
| 5,693,055 A | 12/1997 | Zahiri et al. |
| 5,702,396 A | 12/1997 | Hoenig et al. |
| 5,702,399 A | 12/1997 | Kilpela et al. |
| 5,709,682 A | 1/1998 | Medoff |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,728,099 A | 3/1998 | Tellman et al. |
| 5,733,287 A | 3/1998 | Tepic et al. |
| 5,735,853 A | 4/1998 | Olerud |
| 5,741,256 A | 4/1998 | Bresina |
| 5,741,258 A | 4/1998 | Klaue et al. |
| 5,743,912 A | 4/1998 | Lahille et al. |
| 5,749,872 A | 5/1998 | Kyle et al. |
| 5,766,175 A | 6/1998 | Martinotti |
| 5,772,662 A | 6/1998 | Chapman et al. |
| 5,779,706 A | 7/1998 | Tschakaloff |
| 5,785,713 A | 7/1998 | Jobe |
| 5,797,916 A | 8/1998 | McDowell |
| 5,800,553 A | 9/1998 | Albrektsson et al. |
| 5,810,821 A | 9/1998 | Vandewalle |
| 5,810,822 A | 9/1998 | Mortier |
| 5,810,823 A | 9/1998 | Klaue et al. |
| 5,827,286 A | 10/1998 | Incavo et al. |
| 5,853,413 A | 12/1998 | Carter et al. |
| 5,921,988 A | 7/1999 | Legrand |
| 5,928,084 A | 7/1999 | Green |
| 5,931,801 A | 8/1999 | Burbank et al. |
| 5,931,839 A | 8/1999 | Medoff |
| 5,938,664 A | 8/1999 | Winquist et al. |
| 5,954,722 A | 9/1999 | Bono |
| 5,961,524 A | 10/1999 | Crombie |
| 5,968,046 A | 10/1999 | Castleman |
| 5,968,047 A | 10/1999 | Reed |
| 5,973,223 A | 10/1999 | Tellman et al. |
| 5,976,139 A | 11/1999 | Bramlet |
| 5,976,141 A | 11/1999 | Haag et al. |
| 5,989,255 A | 11/1999 | Pepper et al. |
| 5,999,940 A | 12/1999 | Ranger |
| 6,001,099 A | 12/1999 | Huebner |
| 6,007,535 A | 12/1999 | Rayhack et al. |
| 6,022,352 A | 2/2000 | Vandewalle |
| 6,030,162 A | 2/2000 | Huebner |
| 6,030,389 A | 2/2000 | Wagner et al. |
| 6,059,785 A | 5/2000 | Schavan et al. |
| 6,066,141 A | 5/2000 | Dall et al. |
| 6,096,040 A | 8/2000 | Esser |
| 6,113,603 A | 9/2000 | Medoff |
| 6,129,728 A | 10/2000 | Schumacher et al. |
| 6,129,730 A | 10/2000 | Bono et al. |
| 6,152,927 A | 11/2000 | Farris et al. |
| 6,155,756 A | 12/2000 | Mericle et al. |
| 6,183,474 B1 | 2/2001 | Bramlet et al. |
| 6,183,475 B1 | 2/2001 | Lester et al. |
| 6,187,007 B1 | 2/2001 | Frigg et al. |
| 6,206,881 B1 | 3/2001 | Frigg et al. |
| 6,221,073 B1 | 4/2001 | Weiss et al. |
| 6,221,075 B1 | 4/2001 | Toermala et al. |
| D443,060 S | 5/2001 | Benirschke et al. |
| 6,224,602 B1 | 5/2001 | Hayes |
| 6,228,085 B1 | 5/2001 | Theken et al. |
| 6,235,032 B1 | 5/2001 | Link |
| 6,235,033 B1 | 5/2001 | Brace et al. |
| 6,258,250 B1 | 7/2001 | Weissenbacher et al. |
| 6,261,291 B1 | 7/2001 | Talaber et al. |
| 6,283,969 B1 | 9/2001 | Grusin et al. |
| 6,287,309 B1 | 9/2001 | Baccelli et al. |
| 6,290,703 B1 | 9/2001 | Ganem |
| 6,306,136 B1 | 10/2001 | Baccelli |
| 6,306,140 B1 | 10/2001 | Siddiqui |
| 6,322,562 B1 | 11/2001 | Wolter |
| 6,325,803 B1 | 12/2001 | Schumacher et al. |
| 6,338,734 B1 | 1/2002 | Burke et al. |
| 6,342,055 B1 | 1/2002 | Eisermann et al. |
| 6,348,052 B1 | 2/2002 | Sammarco |
| 6,350,265 B1 | 2/2002 | Blaustein et al. |
| 6,355,041 B1 | 3/2002 | Martin |
| 6,355,042 B2 | 3/2002 | Winquist et al. |
| 6,358,250 B1 | 3/2002 | Orbay |
| 6,364,882 B1 | 4/2002 | Orbay |
| 6,375,657 B1 | 4/2002 | Doubler et al. |
| 6,379,359 B1 | 4/2002 | Dahners |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,423,064 B1 | 7/2002 | Kluger |
| 6,440,131 B1 | 8/2002 | Haidukewych |
| 6,440,135 B2 | 8/2002 | Orbay et al. |
| D463,557 S | 9/2002 | Bryant et al. |
| D463,558 S | 9/2002 | Bryant et al. |
| D463,559 S | 9/2002 | Bryant et al. |
| 6,454,769 B2 | 9/2002 | Wagner et al. |
| 6,454,770 B1 | 9/2002 | Klaue |
| D464,136 S | 10/2002 | Bryant et al. |
| D464,731 S | 10/2002 | Bryant et al. |
| 6,468,278 B1 | 10/2002 | Muckter |
| 6,488,685 B1 | 12/2002 | Manderson |
| D469,532 S | 1/2003 | Bryant et al. |
| D469,533 S | 1/2003 | Bryant et al. |
| D469,534 S | 1/2003 | Bryant et al. |
| 6,503,252 B2 | 1/2003 | Hansson |
| 6,503,281 B1 | 1/2003 | Mallory |
| 6,508,819 B1 | 1/2003 | Orbay |
| D469,874 S | 2/2003 | Bryant et al. |
| D469,875 S | 2/2003 | Bryant et al. |
| D470,588 S | 2/2003 | Bryant et al. |
| 6,525,525 B1 | 2/2003 | Azinger |
| 6,527,776 B1 | 3/2003 | Michelson |
| 6,533,789 B1 | 3/2003 | Hall et al. |
| 6,565,525 B1 | 5/2003 | Burbank et al. |
| 6,565,569 B1 | 5/2003 | Assaker et al. |
| 6,575,975 B2 | 6/2003 | Brace et al. |
| 6,602,256 B1 | 8/2003 | Hayes |
| 6,605,090 B1 | 8/2003 | Trieu et al. |
| D479,331 S | 9/2003 | Pike et al. |
| D480,141 S | 9/2003 | Benirschke et al. |
| 6,623,486 B1 | 9/2003 | Weaver et al. |
| 6,648,891 B2 | 11/2003 | Kim |
| 6,666,868 B2 | 12/2003 | Fallin |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |

(56) References Cited

U.S. PATENT DOCUMENTS

| | | |
|---|---|---|
| 6,730,091 B1 | 5/2004 | Pfefferle et al. |
| 6,767,351 B2 | 7/2004 | Orbay et al. |
| 6,835,197 B2 | 12/2004 | Roth et al. |
| 6,863,483 B2 | 3/2005 | Koenig et al. |
| 6,866,665 B2 | 3/2005 | Orbay |
| 6,875,215 B2 | 4/2005 | Taras et al. |
| 6,893,443 B2 | 5/2005 | Frigg et al. |
| 6,955,677 B2 | 10/2005 | Dahners |
| 6,974,461 B1 | 12/2005 | Wolter |
| 7,001,388 B2 | 2/2006 | Orbay et al. |
| 7,044,953 B2 | 5/2006 | Capanni |
| 7,128,744 B2 | 10/2006 | Weaver et al. |
| 7,169,149 B1 | 1/2007 | Hajianpour |
| 7,179,260 B2 | 2/2007 | Gerlach et al. |
| 7,229,445 B2 | 6/2007 | Hayeck et al. |
| 7,282,053 B2 | 10/2007 | Orbay |
| 7,294,130 B2 | 11/2007 | Orbay |
| 7,309,340 B2 | 12/2007 | Fallin et al. |
| 7,316,687 B2 | 1/2008 | Aikins et al. |
| 7,338,491 B2 | 3/2008 | Baker et al. |
| 7,341,589 B2 | 3/2008 | Weaver et al. |
| 7,354,441 B2 | 4/2008 | Frigg |
| 7,517,350 B2 | 4/2009 | Weiner et al. |
| 7,527,639 B2 | 5/2009 | Orbay et al. |
| 7,537,596 B2 | 5/2009 | Jensen |
| 7,635,381 B2 | 12/2009 | Orbay |
| 7,637,928 B2 | 12/2009 | Fernandez |
| 7,641,677 B2 | 1/2010 | Weiner et al. |
| 7,695,472 B2 | 4/2010 | Young |
| 7,695,502 B2 | 4/2010 | Orbay et al. |
| 7,766,916 B2 | 8/2010 | Leyden et al. |
| 7,771,433 B2 | 8/2010 | Orbay et al. |
| 7,771,457 B2 | 8/2010 | Kay et al. |
| 7,776,076 B2 | 8/2010 | Grady |
| 7,776,916 B2 | 8/2010 | Freeman et al. |
| 7,857,838 B2 | 12/2010 | Orbay |
| 7,867,260 B2 | 1/2011 | Meyer et al. |
| 7,905,909 B2 | 3/2011 | Orbay et al. |
| 7,951,176 B2 | 5/2011 | Grady et al. |
| 8,075,561 B2 | 12/2011 | Wolter |
| 8,092,505 B2 | 1/2012 | Sommers |
| 8,118,846 B2 | 2/2012 | Leither et al. |
| 8,118,848 B2 | 2/2012 | Ducharme et al. |
| 8,337,535 B2 | 12/2012 | White et al. |
| 8,343,196 B2 | 1/2013 | Schneider |
| 8,403,967 B2 | 3/2013 | Orbay |
| 8,506,607 B2 | 8/2013 | Eckhof et al. |
| 8,518,042 B2 | 8/2013 | Winslow et al. |
| 8,556,945 B2 | 10/2013 | Orbay |
| 8,574,268 B2 | 11/2013 | Chan et al. |
| 8,579,946 B2 | 11/2013 | Orbay |
| 8,641,744 B2 | 2/2014 | Weaver et al. |
| 8,758,346 B2 | 6/2014 | Koay et al. |
| 8,814,918 B2 | 8/2014 | Orbay et al. |
| 8,845,698 B2 | 9/2014 | Schneider |
| 8,852,245 B2 | 10/2014 | Schneider |
| 8,876,873 B2 | 11/2014 | Schneider |
| 8,894,693 B2 | 11/2014 | Petit et al. |
| 8,940,029 B2 | 1/2015 | Leung et al. |
| 9,072,558 B2 | 7/2015 | Orbay |
| 9,101,423 B2 * | 8/2015 | Hulliger ............ A61B 17/8057 |
| 9,107,711 B2 | 8/2015 | Hainard |
| 9,168,075 B2 | 10/2015 | Dell Oca |
| 9,265,542 B2 | 2/2016 | Koay et al. |
| 9,277,947 B2 | 3/2016 | Koay et al. |
| 9,295,505 B2 | 3/2016 | Schneider |
| 9,308,034 B2 | 4/2016 | Grady |
| 9,314,284 B2 | 4/2016 | Chan et al. |
| 9,387,022 B2 | 7/2016 | Koay et al. |
| 9,433,454 B2 | 9/2016 | Paolino et al. |
| 9,498,267 B2 | 11/2016 | Pfeiffer et al. |
| 9,510,880 B2 | 12/2016 | Terrill et al. |
| 9,554,909 B2 | 1/2017 | Donner et al. |
| 9,603,641 B2 * | 3/2017 | Hulliger ............ A61B 17/8057 |
| 9,855,083 B2 | 1/2018 | Mighell et al. |
| 9,867,643 B2 | 1/2018 | Terrill et al. |
| 9,931,148 B2 | 4/2018 | Grady |
| 2001/0000186 A1 | 4/2001 | Bramlet et al. |
| 2001/0011172 A1 | 8/2001 | Orbay et al. |
| 2001/0012940 A1 | 8/2001 | Tunc |
| 2002/0013587 A1 | 1/2002 | Winquist et al. |
| 2002/0032446 A1 | 3/2002 | Orbay |
| 2002/0045901 A1 | 4/2002 | Wagner et al. |
| 2002/0049445 A1 | 4/2002 | Hall et al. |
| 2002/0062127 A1 | 5/2002 | Schumacher et al. |
| 2002/0065516 A1 | 5/2002 | Winquist et al. |
| 2002/0128654 A1 | 9/2002 | Steger et al. |
| 2002/0143337 A1 | 10/2002 | Orbay et al. |
| 2002/0143338 A1 | 10/2002 | Orbay et al. |
| 2002/0156474 A1 | 10/2002 | Wack et al. |
| 2002/0183752 A1 | 12/2002 | Steiner et al. |
| 2002/0183753 A1 | 12/2002 | Manderson |
| 2003/0040748 A1 | 2/2003 | Aikins et al. |
| 2003/0055435 A1 | 3/2003 | Barrick |
| 2003/0060827 A1 | 3/2003 | Coughln |
| 2003/0083660 A1 | 5/2003 | Orbay |
| 2003/0083661 A1 | 5/2003 | Orbay et al. |
| 2003/0105461 A1 | 6/2003 | Putnam |
| 2003/0125738 A1 | 7/2003 | Khanna |
| 2003/0135212 A1 | 7/2003 | Y Chow |
| 2003/0135216 A1 | 7/2003 | Sevrain |
| 2004/0030339 A1 | 2/2004 | Wack et al. |
| 2004/0049193 A1 | 3/2004 | Capanni |
| 2004/0059334 A1 | 3/2004 | Synthes |
| 2004/0059335 A1 | 3/2004 | Weaver et al. |
| 2004/0073218 A1 | 4/2004 | Dahners |
| 2004/0097937 A1 | 5/2004 | Pike et al. |
| 2004/0097941 A1 | 5/2004 | Weiner et al. |
| 2004/0111089 A1 | 6/2004 | Stevens et al. |
| 2004/0215198 A1 | 10/2004 | Marnay et al. |
| 2004/0254579 A1 | 12/2004 | Buhren et al. |
| 2004/0260291 A1 | 12/2004 | Jensen |
| 2004/0260306 A1 | 12/2004 | Fallin et al. |
| 2005/0015089 A1 | 1/2005 | Young et al. |
| 2005/0049593 A1 | 3/2005 | Duong et al. |
| 2005/0080421 A1 | 4/2005 | Weaver et al. |
| 2005/0085818 A1 | 4/2005 | Huebner |
| 2005/0107796 A1 | 5/2005 | Gerlach et al. |
| 2005/0165400 A1 | 7/2005 | Fernandez |
| 2005/0171544 A1 | 8/2005 | Falkner, Jr. |
| 2005/0187555 A1 | 8/2005 | Biedermann et al. |
| 2005/0216001 A1 | 9/2005 | David |
| 2005/0261688 A1 | 11/2005 | Grady et al. |
| 2005/0277937 A1 | 12/2005 | Leung et al. |
| 2006/0004361 A1 | 1/2006 | Hayeck et al. |
| 2006/0009771 A1 | 1/2006 | Orbay et al. |
| 2006/0058797 A1 | 3/2006 | Mathieu et al. |
| 2006/0200151 A1 | 9/2006 | Ducharme et al. |
| 2006/0217722 A1 | 9/2006 | Dutoit et al. |
| 2006/0235400 A1 | 10/2006 | Schneider |
| 2006/0264946 A1 | 11/2006 | Young |
| 2007/0016205 A1 | 1/2007 | Beutter et al. |
| 2007/0083207 A1 | 4/2007 | Ziolo et al. |
| 2007/0088360 A1 | 4/2007 | Orbay et al. |
| 2007/0162016 A1 | 7/2007 | Matityahu |
| 2007/0206244 A1 | 9/2007 | Kobayashi |
| 2007/0208378 A1 | 9/2007 | Bonutti et al. |
| 2007/0225716 A1 | 9/2007 | Deffenbaugh et al. |
| 2007/0260244 A1 | 11/2007 | Wolter |
| 2007/0276386 A1 | 11/2007 | Gerlach et al. |
| 2007/0276402 A1 | 11/2007 | Frankel et al. |
| 2008/0065070 A1 | 3/2008 | Freid et al. |
| 2008/0132960 A1 | 6/2008 | Weaver et al. |
| 2008/0140130 A1 | 6/2008 | Chan et al. |
| 2008/0208259 A1 | 8/2008 | Gilbert et al. |
| 2008/0234749 A1 * | 9/2008 | Forstein ............ A61B 17/8057 606/291 |
| 2008/0234752 A1 | 9/2008 | Dahners |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0036933 A1 | 2/2009 | Dube et al. |
| 2009/0076553 A1 | 3/2009 | Wolter |
| 2009/0076554 A1 | 3/2009 | Huebner et al. |

(56) References Cited

U.S. PATENT DOCUMENTS

| | | |
|---|---|---|
| 2009/0099610 A1 | 4/2009 | Johnson et al. |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0216242 A1 | 8/2009 | Riemer et al. |
| 2009/0281543 A1 | 11/2009 | Orbay et al. |
| 2009/0287258 A1 | 11/2009 | Vannemreddy |
| 2009/0292318 A1 | 11/2009 | White et al. |
| 2009/0312803 A1 | 12/2009 | Austin et al. |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |
| 2010/0312285 A1 | 12/2010 | White et al. |
| 2010/0312286 A1 | 12/2010 | Dell Oca |
| 2011/0046681 A1 | 2/2011 | Prandi et al. |
| 2011/0087229 A1 | 4/2011 | Kubiak et al. |
| 2011/0106081 A1 | 5/2011 | Graham et al. |
| 2011/0224671 A1 | 9/2011 | Koay et al. |
| 2011/0301608 A1 | 12/2011 | Roth et al. |
| 2012/0143193 A1 | 6/2012 | Hulliger |
| 2012/0197307 A1 | 8/2012 | Fritzinger et al. |
| 2012/0245642 A1 | 9/2012 | Giannoudis et al. |
| 2013/0096631 A1 | 4/2013 | Leung et al. |
| 2013/0116735 A1 | 5/2013 | Schneider |
| 2013/0172943 A1 | 7/2013 | Austin et al. |
| 2013/0190828 A1 | 7/2013 | Schneider |
| 2013/0197589 A1 | 8/2013 | Schneider |
| 2013/0245699 A1 | 9/2013 | Orbay et al. |
| 2013/0261675 A1 | 10/2013 | Fritzinger |
| 2014/0005728 A1 | 1/2014 | Koay et al. |
| 2014/0018862 A1 | 1/2014 | Koay et al. |
| 2014/0180345 A1 | 6/2014 | Fernandez |
| 2014/0207194 A1 | 7/2014 | Wolter |
| 2014/0236154 A1 | 8/2014 | Liao et al. |
| 2014/0271028 A1 | 9/2014 | Arnett |
| 2014/0277180 A1 | 9/2014 | Paolino et al. |
| 2014/0316473 A1 | 10/2014 | Pfeiffer et al. |
| 2014/0324108 A1 | 10/2014 | Orbay et al. |
| 2015/0051651 A1 | 2/2015 | Terrill et al. |
| 2015/0105829 A1 | 4/2015 | Laird |
| 2015/0257802 A1 | 9/2015 | Wolf et al. |
| 2015/0327897 A1 | 11/2015 | Hulliger |
| 2015/0327898 A1 | 11/2015 | Martin |
| 2015/0359575 A1 | 12/2015 | Pech et al. |
| 2016/0074081 A1 | 3/2016 | Weaver et al. |
| 2016/0089191 A1 | 3/2016 | Pak et al. |
| 2016/0143676 A1 | 5/2016 | Koay et al. |
| 2016/0166294 A1 | 6/2016 | Schneider |
| 2016/0242829 A1 | 8/2016 | Kim et al. |
| 2016/0278826 A1 | 9/2016 | Epperly |
| 2016/0310184 A1 | 10/2016 | Kazanovicz et al. |
| 2016/0317205 A1 | 11/2016 | Baker |
| 2016/0367299 A1 | 12/2016 | Paolino et al. |
| 2017/0265915 A1 | 9/2017 | Langdale et al. |
| 2017/0319248 A1 | 11/2017 | Milella et al. |
| 2018/0008326 A1 | 1/2018 | Hulliger et al. |
| 2018/0036049 A1 | 2/2018 | Kobayashi |
| 2018/0064477 A1 | 3/2018 | Lopez et al. |
| 2018/0064479 A1 | 3/2018 | Lopez et al. |
| 2018/0132913 A1 | 5/2018 | Davison et al. |
| 2018/0235681 A1 | 8/2018 | Chambers et al. |
| 2019/0298426 A1 | 10/2019 | Bosshard et al. |

FOREIGN PATENT DOCUMENTS

| | | |
|---|---|---|
| CA | 2536960 A1 | 3/2005 |
| CH | 611147 A5 | 5/1979 |
| CH | 670755 A5 | 7/1989 |
| CH | 672245 A5 | 11/1989 |
| CH | 675531 A5 | 10/1990 |
| CN | 1486162 A | 3/2004 |
| DE | 2933637 A1 | 4/1980 |
| DE | 3442004 C1 | 4/1986 |
| DE | 3722852 A1 | 1/1989 |
| DE | 3743638 A1 | 7/1989 |
| DE | 4004941 A1 | 8/1990 |
| DE | 3942326 A1 | 6/1991 |
| DE | 4201531 A1 | 7/1993 |
| DE | 4341980 A1 | 6/1995 |
| DE | 4343117 A1 | 6/1995 |
| DE | 4438264 A1 | 3/1996 |
| DE | 19636733 A1 | 4/1997 |
| DE | 19629011 A1 | 1/1998 |
| DE | 9321544 U1 | 9/1999 |
| DE | 19832513 A1 | 2/2000 |
| DE | 19858889 A1 | 6/2000 |
| DE | 10015734 A1 | 9/2001 |
| DE | 10125092 A1 | 12/2001 |
| DE | 20309361 U1 | 9/2003 |
| DE | 20317651 U1 | 3/2004 |
| DE | 10319781 B3 | 8/2004 |
| DE | 102004009429 A1 | 9/2005 |
| DE | 102005042766 A1 | 1/2007 |
| DE | 202006019220 U1 | 5/2007 |
| DE | 202008000914 U1 | 3/2008 |
| DE | 202007017159 U1 | 5/2008 |
| DE | 102010048052 | 4/2012 |
| DE | 102016112845 A1 | 1/2018 |
| DE | 202014011161 U1 | 3/2018 |
| EP | 0053999 A1 | 6/1982 |
| EP | 0158030 A1 | 10/1985 |
| EP | 0180532 A1 | 5/1986 |
| EP | 0207884 A2 | 1/1987 |
| EP | 0241914 A2 | 10/1987 |
| EP | 0244782 A1 | 11/1987 |
| EP | 0251583 A2 | 1/1988 |
| EP | 0266146 A2 | 5/1988 |
| EP | 0274713 A1 | 7/1988 |
| EP | 0290138 A2 | 11/1988 |
| EP | 0291632 A1 | 11/1988 |
| EP | 0299160 A1 | 1/1989 |
| EP | 0337288 A1 | 10/1989 |
| EP | 0360139 A2 | 3/1990 |
| EP | 0381462 A2 | 8/1990 |
| EP | 0382256 A1 | 8/1990 |
| EP | 0410309 A1 | 1/1991 |
| EP | 0436885 A2 | 7/1991 |
| EP | 0471418 A1 | 2/1992 |
| EP | 0506420 A1 | 9/1992 |
| EP | 0515828 A1 | 12/1992 |
| EP | 0530585 A2 | 3/1993 |
| EP | 0532421 A1 | 3/1993 |
| EP | 0546460 A1 | 6/1993 |
| EP | 0649635 A1 | 4/1995 |
| EP | 0668059 A1 | 8/1995 |
| EP | 0760231 A1 | 3/1997 |
| EP | 0848600 A1 | 6/1998 |
| EP | 1132052 A2 | 9/2001 |
| EP | 1468655 A2 | 10/2004 |
| EP | 1604619 A1 | 12/2005 |
| EP | 1658015 A1 | 5/2006 |
| EP | 1712197 A1 | 10/2006 |
| EP | 1741397 A2 | 1/2007 |
| EP | 1767160 A2 | 3/2007 |
| EP | 1878394 A2 | 1/2008 |
| EP | 1568329 A1 | 8/2008 |
| EP | 2529685 A1 | 12/2012 |
| FR | 0742618 A | 3/1933 |
| FR | 2233973 A1 | 1/1975 |
| FR | 2405062 A1 | 5/1979 |
| FR | 2405705 A1 | 5/1979 |
| FR | 2405706 A1 | 5/1979 |
| FR | 2496429 A3 | 6/1982 |
| FR | 2606268 A1 | 5/1988 |
| FR | 2622431 A1 | 5/1989 |
| FR | 2650500 A1 | 2/1991 |
| FR | 2671966 A3 | 7/1992 |
| FR | 2674118 A1 | 9/1992 |
| FR | 2677876 A1 | 12/1992 |

(56) References Cited

FOREIGN PATENT DOCUMENTS

| | | |
|---|---|---|
| FR | 2706763 A1 | 12/1994 |
| FR | 2739151 A1 | 3/1997 |
| FR | 2757370 A1 | 6/1998 |
| FR | 2802082 A1 | 6/2001 |
| GB | 0997733 A | 7/1965 |
| GB | 1237405 A | 6/1971 |
| GB | 1250413 A | 10/1971 |
| GB | 1312189 A | 4/1973 |
| GB | 1385398 A | 2/1975 |
| GB | 2017502 A | 10/1979 |
| GB | 1575194 A | 9/1980 |
| GB | 2090745 A | 7/1982 |
| GB | 2245498 A | 1/1992 |
| GB | 2257913 A | 1/1993 |
| JP | 02-121652 A | 5/1990 |
| JP | 03-058150 | 3/1991 |
| JP | 03-158150 | 7/1991 |
| JP | 04-138152 A | 5/1992 |
| JP | 06-045941 | 2/1994 |
| JP | 06-125918 | 5/1994 |
| JP | 06-245941 | 9/1994 |
| JP | 08-098846 | 4/1996 |
| JP | 08-126650 | 5/1996 |
| JP | 08-257034 | 10/1996 |
| JP | 08-266562 A | 10/1996 |
| JP | 09-108237 | 4/1997 |
| JP | 10-118096 A | 5/1998 |
| JP | 11-076259 | 3/1999 |
| JP | 11-299804 | 8/1999 |
| JP | 11-276501 | 10/1999 |
| JP | 11-512004 | 10/1999 |
| JP | 11-318930 | 11/1999 |
| JP | 2000-000247 A | 1/2000 |
| JP | 2000-152944 A | 6/2000 |
| JP | 2001-149379 A | 6/2001 |
| JP | 2001-161704 A | 6/2001 |
| JP | 2001-514039 | 9/2001 |
| JP | 2001-525701 | 12/2001 |
| JP | 2001-525702 | 12/2001 |
| JP | 2002-095673 A | 4/2002 |
| JP | 2002-232185 A | 8/2002 |
| JP | 2002-532185 A | 10/2002 |
| JP | 2002-345836 A | 12/2002 |
| JP | 2002-542875 | 12/2002 |
| JP | 2003-024344 A | 1/2003 |
| JP | 2003-038508 A | 2/2003 |
| JP | 2003-038509 A | 2/2003 |
| JP | 2003-509107 | 3/2003 |
| JP | 2003-521303 | 7/2003 |
| KR | 10-2007-0034449 A | 3/2007 |
| KR | 10-2008-0028917 A | 4/2008 |
| SU | 1037911 | 8/1983 |
| SU | 1279626 | 12/1986 |
| WO | 87/00419 A1 | 1/1987 |
| WO | 87/06982 A1 | 11/1987 |
| WO | 88/03781 A1 | 6/1988 |
| WO | 92/11819 A1 | 7/1992 |
| WO | 93/11714 A1 | 6/1993 |
| WO | 93/15678 A1 | 8/1993 |
| WO | 93/22982 A1 | 11/1993 |
| WO | 94/02073 A1 | 2/1994 |
| WO | 95/32674 A1 | 12/1995 |
| WO | 96/17556 A1 | 6/1996 |
| WO | 96/25892 A1 | 8/1996 |
| WO | 96/29948 A1 | 10/1996 |
| WO | 97/08999 A1 | 3/1997 |
| WO | 97/09000 A1 | 3/1997 |
| WO | 97/20514 A1 | 6/1997 |
| WO | 98/02105 A1 | 1/1998 |
| WO | 98/05263 A1 | 2/1998 |
| WO | 98/51226 A2 | 11/1998 |
| WO | 98/51368 A1 | 11/1998 |
| WO | 99/25266 A1 | 5/1999 |
| WO | 99/44529 A1 | 9/1999 |
| WO | 00/53110 A1 | 9/2000 |
| WO | 00/53111 A1 | 9/2000 |
| WO | 00/66012 A1 | 11/2000 |
| WO | 01/19267 A1 | 3/2001 |
| WO | 01/19268 A1 | 3/2001 |
| WO | 01/26566 | 4/2001 |
| WO | 01/54601 A1 | 8/2001 |
| WO | 01/89400 A2 | 11/2001 |
| WO | 02/71963 | 9/2002 |
| WO | 02/96309 A1 | 12/2002 |
| WO | 03/02856 | 1/2003 |
| WO | 03/22166 | 3/2003 |
| WO | 03/28567 | 4/2003 |
| WO | 03/57055 | 7/2003 |
| WO | 2004/043277 A1 | 5/2004 |
| WO | 2004/089233 A1 | 10/2004 |
| WO | 2004/107957 A2 | 12/2004 |
| WO | 2005/018472 A1 | 3/2005 |
| WO | 2005/044121 A1 | 5/2005 |
| WO | 2007/014279 A2 | 2/2007 |
| WO | 2007/108734 A1 | 9/2007 |
| WO | 2009/023666 A2 | 2/2009 |
| WO | 2009/058969 A1 | 5/2009 |
| WO | 2011/032140 A1 | 3/2011 |
| WO | 20121112327 A2 | 8/2012 |
| WO | 20131045713 A1 | 4/2013 |
| WO | 20171048909 A1 | 3/2017 |

OTHER PUBLICATIONS

U.S. Appl. No. 15/926,390, Bone Plate With Form-Fitting Variable-Angle Locking Hole, filed Mar. 20, 2018.

Zimmer Advertisement, J. of Orthopaedic Trauma, vol. 12, No. 5, Jun./Jul. 1998.

Vattolo, M., Thesis, "The Effect of Grooves in Osteosynthesis Plates on the Restructuring of the Corticalis," Laboratory for Experimental Surgery, Swiss Research Institute, 1986 (original in German, translation to English attached with Certification).

Update, Titanium LC-DCP Condylar Buttress Plate, Jun. 15, 1995 (Synthes) ("The LC-DCP update").

Universelle Rekonstruktionsplatte URP 2.4-3.2 (UniRecon-Registered), Swiss Dent, 17, 1996, pp. 19-25.

The Titanium Distal Radius Plate Technique Guide, published by Synthes, 1997.

The Titanium Distal Radius Plate Technique Guide, (the "DRp Guide") published by Synthes in 1996.

The Locking Reconstruction Plate Technique Guide, published by Synthes, 1997.

The Distal Radius Plate Instrument and Implant Set Technique Guide, (Synthes) ("1999 Radius Plate Guide").

The Distal Radius Plate Instrument and Implant Set Technique Guide, (Synthes) ("1998 Radius Plate Guide").

The 1998 Schuhli Guide.

Technique Guide: 2.4 mm Variable Angle LCP Distal Radius System. Synthes, 2008, 43 pages.

Technique Guide, Less Invasive Stabilization (LISS), Oct. 2003.

Synthes' Supporting Memorandum for Reconsideration of Claim Construction (without supporting Declaration) in the Pennsylvania Action, dated Feb. 19, 2008.

Synthes' Summary Judgment Motion of no. Invalidity Based on K982222 Summary including supporting memorandum, and declarations of A. Silversti and B. Liu (with supporting exhibits), dated Sep. 10, 2008.

Synthes' Responsive Claim Construction Brief (without exhibits) for the Pennsylvania Action, dated Apr. 20, 2007.

Synthes' Response to Smith & Nephew's Statement of Facts in Support of Smith & Nephew's Motion for Summary Judgment of Invalidity of the '744 patent; dated Sep. 29, 2008; 19 pages.

Synthes' Response to Motion for Leave to Amend Answer, Civil Action No. 03-0084 (E.D. Pa.), dated Aug. 9,2007.

Synthes' Reply to Smith & Nephew's Opposition to Synthes Motion for Reconsideration of Claim Construction for the '486 patent in the Pennsylvania Action, dated Mar. 14, 2008.

Synthes' Opposition to Smith & Nephew's Motion for Summary Judgment of Invalidity of the '744 patent; dated Sep. 29, 2008; 22 pages.

(56) References Cited

OTHER PUBLICATIONS

Synthes' Opening Claim Construction Brief (without supporting declaration and attached exhibits but including Appendix A & B) for the Pennsylvania Action, dated Mar. 16, 2007 (Dkt. 54) (Ex. 5).
Synthes' 1996 Titanium Modular Hand System brochure (the "Hand System Brochure") [SNI-0290287-294] (Ex. 47).
Synthes Titanium Modular Hand System, 1996.
Synthes Opposition to Smith & Nephew's Motion for Summary Judgment of Invalidity of Claims 10-12 of the '486 Patent, dated Sep. 29, 2008 (Dkt. 159) (Ex 67).
Synthes 1997 Catalog, published by Synthes, Mar. 1997; part 2, 261 pgs.
Synthes 1997 Catalog, published by Synthes, Mar. 1997; part 1, 200 pgs.
Sutter, F., et al., "Titanplasma-beschichtetes Hohlschrauben- und Rekonstructions-platten-System (THRP) zur Oberbriickung van Kieferdefekten," Chirurg No. 55, pp. 741-748, 1984 [SNI-0006164-171], and translation thereof [SNI-0006152-163] (Ex. 33).
Surgical Instruments Catalog, Collin & Co., 1935 (original in French, translation to English of pp. 392-397 attached with certification).
Supplemental Expert Report of Clifford H. Turen, M.D., May 2009 (with Exhibit 1), dated Aug. 8, 2008(Ex.60).
Supplement to Apr. 9, 2008 Expert Report of John F. Witherspoon (without exhibits), dated May 14, 2008 (Ex. 74).
Supplement to Apr. 9, 2008 Expert Report of J. Lawrence Marsh in the Pennsylvania Action (with Exhibit 1), dated May 14, 2008 (Ex. 46).
Summary of Safety and Effectiveness Information [510(k) Summary], K982222, Jul. 29, 1998.
Stay Order in Pennsylvania Action, dated Jul. 13, 2009.
Smith and Nephew's Opposition to Synthes Motion for Summary Judgment of No Invalidity Based on K982222(including Opposition Memorandum, Statement of Undisputed Facts, K. Doyle Declaration with Exhibits A-F and R. King's Declaration with Exhibits A-D), dated Sep. 29, 2008( Dkt. 154) (Ex. 63).
Smith & Newphew Statement of Undisputed Facts in Support of its Motion for Summary Judgment of Invalidity of U.S. Pat. No. 7,128,744; dated Sep. 29, 2008; 8 pages.
*Smith & Nephew, Inc. v. Rea*, Federal Circuit Opinion dated Jul. 9, 2013, 18 pages.
Smith & Nephew's Third Supplemental Response to Interrogatories Nos. 4, 5, 6, 8 and 9; Second Supplemental Responses to Interrogatories Nos. 1, 2, 3, 10, 11 and 12; and First Supplemental Responses to Interrogatories Nos. 13, 15 and 17 (with Smith & Nephew Exhibit 1 thereto), dated Aug. 11, 2008 (Ex. 14).
Smith & Nephew's Responsive Claim Construction Brief (without exhibits) for the Pennsylvania Action, dated Apr. 20, 2007 (Dkt. 60) (Ex. 8).
Smith & Nephew's Responses and Objections to Plaintiffs Fourth Set of Interrogatories Nos. 15-16, dated May 21, 2008 (Ex. 55).
Smith & Nephew's Opposition to Synthes' Motion for Reconsideration of Claim Construction for the '486 Patent in the Pennsylvania Action, dated Mar. 4, 2008 (Dkt. 108) (Ex. 11).
Smith & Nephew's Opening Claim Construction Brief (without exhibits) for the Pennsylvania Action, dated Mar. 16, 2007 (Dkt. 53) (Ex. 6).
Smith & Nephew's Memorandum in Support of Motion for Leave to file Amended Answer in the Pennsylvania Action, dated Aug. 7, 2007 (Dkt. 77) (Ex. 70).
Smith & Nephew's Memorandum in Support of its Motion for Summary Judgment of Invalidly of U.S. Pat. No. 7,128,744; dated Sep. 10, 2008; 22 pages.
Smith & Nephew's Memorandum in Support of its Motion for Partial Summary Judgment of Invalidity of Claims 10-12 of the '486 patent, dated Sep. 10, 2008.
Smith & Nephew's Amended Answer in the Pennsylvania Action (without Exhibits A-S ) in the Pennsylvania Action, dated Aug. 7, 2007.
Smith & Nephew Amended Answer and Counterclaims of Defendant, Civil Action No. 03-0084 (E.D. Pa.), dated Aug. 7, 2007.
Second Supplement to Apr. 9, 2008 Expert Report of J. Lawrence Marsh (with Exhibit 1), dated Sep. 3, 2008.
Second Supplement to Apr. 9, 2008 Expert Report of David Seligson, M.D., dated Sep. 3, 2008.
Schuhli Technique Guide, published by Synthes, 1995.
Schuhli Technique Guide 1998, (Synthes) ("Schuhli Guide").
Schmoker, The Locking Reconstruction Plate 2.4-3.2, originally published in Swiss Dent 17, 1996.
Dr. Turen's Aug. 15, 2008 deposition transcript in the Pennsylvania Action (Ex. 61).
Dr. Parsons Aug. 7, 2008 deposition transcript in the Pennsylvania Action (Ex. 58).
Dr. Marsh's Jul. 26, 2008 Deposition transcript in the Pennsylvania Action (Ex. 52).
Docket sheet for the Pennsylvania Action—2:03-cv-0084 (CDJ) (Ex. 4) filed Jan. 7, 2003.
Docket sheet for the California Action—3:07-cv-00309-L-AJB (Ex. 1) Filed Feb. 14, 2007.
Defendant's Motion for Leave to Amend Answer to Assert Allegations of Inequitable Conduct, Civil Action No. 03-0084 (E.D. Pa.), dated Aug. 7, 2007.
Declaration of Robert A. King in Support of their Motion for Partial Summary Judgment of Invalidity of Claims 10-12 of U.S. Pat. No. 6,623,486 (without exhibits), dated Sep. 10, 2008.
Declaration of J. Russell Parsons, Ph.D. in Support of Synthes Opposition to Smith & Nephew's Motion for Summary Judgement of Invalidity of the '744 patent (wlo Exhibits 1-4) dated Sep. 29, 2008; 15 pages.
Declaration of J. Russell Parsons, Ph.D. in Support of Synthes Opposition to Smith & 179 Nephew's Motion for Partial Summary Judgment of Invalidity of Method Claims 10-12 of U.S. Pat. No. 6,623,486 dated Sep. 26, 2008 (with Exhibits 1-4, pp. 19-105 dated Sep. 29, 2008).
Declaration of J. Lawrence Marsh, M.D. dated Nov. 22, 2010.
Declaration of J. Lawrence Marsh, M.D. dated Jun. 25, 2010.
Declaration of J. Lawrence Marsh, M.D. dated Jun. 3, 2010.
Declaration of Dr. Seligson, M.D. in Support of Smith & Nephew's Motion for Partial Summary 175 Judgment of Invalidity of Claims 10-12 of U.S. Pat. No. 6,623,486 dated Sep. 9, 2008 (with Exhibit 1, pp. 16-66 dated Sep. 10, 2008).
Declaration of Clifford H. Turen, M.D. in Support of Synthes' Opposition to Smith & Nephew's Motion for Partial Summary Judgment of Invalidity of Method Claims 10-12 of U.S. Pal No. 6,623,486 (with Exhibits 1-4 ), dated Sep. 29, 2008.
Declaration of Charles E. Van Horn, Esq., in Support of Synthes Opposition to Smith & Nephew's Motion for Summary Judgement of Invalidity of the 744 patent (w/o Exhibits 1-6) dated Sep. 29, 2008; 12 pages.
Court Order denying Synthes' Motion for Reconsideration of Claim Construction for the '486 Patent in the Pennsylvania Action, dated Jun. 30, 2008.
Collins Instruments de Chirurgie, published 1935, as illustrated at http://www.litos.com/pages/winkelstabilitaet_e.html (Sep. 26, 2007) ("Collin Catalog") [SNI-0258552-556] (Ex. 20).
Claim Construction Order in Pennsylvania Action, dated Feb. 4, 2008.
Brief in Support of Defendants' Motion for Leave to Amend Answer to Assert Allegations of Inequitable Conduct, Civil Action No. 03-0084 (E.D. Pa.), dated Aug. 7, 2007.
Bone Plating System, U.S. Appl. No. 09/660,287.
Bone Fixation Method, U.S. Appl. No. 09/848,251.
Bolhofner, et al., "The Results of Open Reduction and Internal Fixation of Distal Femur Fractures Using a Biologic (Indirect) Reduction Technique," J. of Orthopaedic Trauma, 1996, vol. 10, No. 6, 372-377.
AO/ASIF Instruments and Implants, A Technical Manual, Springer-Verlag, 1994 (the "AO-ASIF Manual").
Answer to Amended Complaint and Counterclaims, Civil Action No. 03-0084 (E .. D. Pa), filed Dec. 5. 2006.
Amended Complaint for Patent Infringement, Civil Action No. 03-0084 (E.D. Pa.), filed Nov. 13, 2006.
ACE Symmetry (Trademark) Titanium Upper Extremity Plates, Ace Medical Company, 6 pages.

(56) References Cited

OTHER PUBLICATIONS

510(k) Summary for Synthes (USA)'s Distal Femur Plate (DFP) System (K982222), dated Jul. 29, 1998 (attached as Exhibit O to Amended Answer).
510(k) Summary for Synthes (USA)'s Anatomical Locking Plate System (K961413), dated Aug. 7, 1996 (attached as Exhibit Q to Amended Answer).
510(k) Summary for Synthes (USA)'s 2.4 mm Universal Locking Plate System (K961421 ), dated Jun. 26, 1996 (attached as Exhibit S to Amended Answer).
510(k) Disclosure K982732, Oct. 8, 1998 (Synthes) ("K982732") [SNI-0259741-744] (Ex. 39).
510(k) Disclosure K963798, Nov. 27, 1996 (Synthes) ("K963798") [SNI-0258398] (Ex. 38).
510(k) Disclosure K962616, Sep. 3, 1996 (Synthes) ("K962616") [SNI-0258397] (Ex. 37).
510(k) Disclosure K961421, Jun. 26, 1996 (Synthes) ("K961421 ") [SNI-0258396] (Ex. 36).
510(k) Disclosure K961413, Aug. 7, 1996 (Synthes) ("K961413") [SNI-0259751] (Ex. 35).
4.5 mm Cannulated Screw Technique Guide, published 1995 (Synthes) [SNI-0259703-714] (Ex. 21).
35 U.S.C..sctn.282 Notice in the Pennsylvania Action, dated Oct. 10, 2008.
"VariAx TM Distal Radius Locking Plate System", Stryker R, Copyright 2009, 12 pages.
"The New Comprehensive Stryker R VariAx TM Distal Radius Locking Plate System", Copyright 2009, 20 pages.
"Less Invasive Stabilization System (LISS) Technique Guide," Synthes (USA) Copyright 2000 (attached as Exhibit K to Amended Answer).
Schandelmaier, et al., Distal Femur Fractures and LISS Stabilization, Injury, Int. J. Care Injured, vol. 32, Suppl. 3, 55-63, 2001.
Ring, D., et al. "Prospective Multicenter Trial of a Plate for Distal Fixation of Distal Radius Fractures," J. of Hand Surgery, vol. 22a(5), pp. 777-784, Sep. 1997.
Ring, D., et al,"A New Plate for Internal Fixation of the Distal Radius," AO.ASIF Dialogue, vol. IX, issue I, Jun. 1996 [SNI-0254971-973] (Ex. 53).
Reply to Counterclaims, Civil Action No. 03-0084 (Ed. Pa.). filed Jan. 2, 2007.
Rebuttal Expert Report of Russell Parsons, Ph.D., (with Exhibit 1), dated Jul. 15, 2008.
Rebuttal Expert Report of Mari Truman, P.E., (with Exhibit 2), dated May 14, 2008 (Ex. 79).
Rebuttal Expert Report of Eric R. Gozna, M.D., P.Eng., (with Exhibit 1), dated May 13, 2008 (Ex. 56).
Rebuttal Expert Report of Clifford H. Turen, M.D., (with Exhibit 1 ), dated May 14, 2008.
Rebuttal Expert Report of Charles E. Van Horn (without Exhibits), dated May 12, 2008 (Ex. 77).
Pure Titanium Implants Catalog, published Dec. 1993 (Synthes) ("PTI") [SN10259670-673] (Ex. 23).
Printout of http://www.aofoundation.org web site, dated May 23, 2007 (attached as Exhibit L to Amended Answer).
Printout from USFDA 510(k) Premarket Notification Database, dated May 23, 2007, listing Synthes Distal Femur Plate (DFP) System, and bearing 510(k) No. K982222 (attached as Exhibit N To Amended Answer.
Printout from USFDA 510(k) Premarket Notification Database, dated May 22, 2007, listing Synthes 2.4 mm Universal Locking Plate System, and bearing 510(k) No. K961421 (attached as Exhibit R to Amended Answer).
Printout from US FDA 510(k) Premarket Notification Database, dated May 22, 2007, listing Synthes Anatomical Locking Plate System, and bearing 510(k) No. K961413 (attached as Exhibit P to Amended Answer).
Photographs of the Pi plate marked as Little Deposition Exhibit 84.
Photographs of the Bolhofner Distal Femur Plating System (Bolhofner DFPS), Apr. 14, 2008.
Photographs of Synthes Titanium Distal Femur LISS Plate, 9 holes/236 mm—Right, 42.344 (the sample LISS)(SYN-PHY-0000002).
Photographs of Synthes Less Invasive Stabilization System (LISS), screw; (SYN-PHY0000004).
Photographs of Sample Synthes LC-DCP Tibia Plate produced as SYN-PHY-0000014.
Photographs of Sample Synthes LC-DCP CBP produced as SYN-PHY-0000011.
Photographs of sample LC-DCP Condylar Buttress Plate ("CBP") [SYN-PHY-0000001] (Ex. 42).
Perren, S., et al., "Early Temporary Porosis of Bone Induced by Internal Fixation Implants," Clinical Orthopaedics and Related Research, No. 232, Jul. 1988, 139-151.
Perren, et al., "The Limited Contact Dynamic Compression Plate (LC-DCP)," Arch. Orthopaedic & Trauma Surg., 1990, vol. 109, 304-310.
Ms. Truman's Jul. 24, 2008 deposition transcript in the Pennsylvania Action (Ex. 81).
Mr. Van Horn's Jul. 15, 2008 deposition transcript in the Pennsylvania Action (Ex. 78).
Marsh Exhibit C, Declaration of J. Lawrence Marsh, MD., in support of Smith & Nephew's, Inc's Motion for Partial Summary Judgement of Invalidity of Claims 10-12 of U.S. Pat. No. 6,623,486, dated Sep. 9, 2008, pp. 1-20.
Marsh Exhibit B, Supplement to Apr. 9, 2008 Expert Report of J. Lawrence Marsh, Md, Civil Action No. 03-0084, dated May 14, 2008 , pp. 1-19.
Marsh Exhibit A, Releasable 510(k) Search, Aug. 7, 2000, http://web.archive.org/web/19970615015534/www.fda.gov/egibin/htmlscript?5-IOk.hts+showcat-OR.
Marsh Exhibit A, Initial Expert Report of J. Lawrence Marsh, MD, Civil Action No. 03-0084, dated Apr. 9 , 2008 , pp. 1-181.
Marsh Exhibit A dated Jun. 25, 2010.
Marsh Exhibit 1, Curriculum Vitae, Dec. 2006, pp. 1-34.
Marsh Exhibit 1, Affidavit of Christopher Butler dated Aug. 24, 2010.
Marsh Exhibit 1 dated Nov. 22, 2010.
Marsh Exhibit 1 dated Jun. 25, 2010.
Manual of Internal Fixation, Techniques Recommended by the AO-ASIG Group, Springer-Verlag, 1991, 200-251.
Luthi, U., et al., "Kontackflache zwischen Osteosyntheseplatte and Knochen," Aktuel. Traumatol. 10:131-136, 1980 ("Luthi") [SNI-0258572-577] (Ex. 31).
Less Invasive Stabilization System LISS Surgical Technique Proximal Tibia, (Draft), 2000, 11 pgs.
Krettek, C., LISS: Less Invasive Stabilization System, AO Dialogue, vol. 12(1), Jun. 1999 ("Krettek").
Krettek et al.; "Distale Femurfrakturen"; Swiss Surg.; 1998; 4; p. 263-278 (No English Translation).
Koval, k., et al., "Distal Femoral Fixation: A Biomechanical Comparison of the Standard Condylar Buttress Plate, a Locked Buttress Plate, and the 95-Degree Blade Plate," J. of Orthopaedic Trauma, val. 11(7), pp. 521-524, Lippencott-Raven Publishers, Oct. 1997.
Kolodziej, P., et al. "Biomechanical Evaluation of the Schuhli Nut," Clinical Orthopaedics and Related Research, No. 34 7, pp. 79-85, Lippencott-Raven Publishers, Feb. 1988 ("Kolodziej") [SNI-0256042-048] (Ex. 28).
Kassab, et al., "Patients Treated for Nonunions with Plate and Screw Fixation and Adjunctive Locking Nuts," Clinical Orthopaedics and Related Research, 1998, 347, 86-92.
Joint submission setting forth agreed claim construction in the Pennsylvania Action, dated Jul. 31, 2007.
Initial Expert Report of J. Lawrence Marsh, M.D., Apr. 9, 2008 (with Exhibits 1-2 and Appendices A-L), dated Apr. 9, 2008 (Ex. 41).
Initial Disclosures of Defendant, Civil Action No. 03-0084 (E.D. Pa), dated Jan. 12, 2007.
Information Disclosure Statement in U.S. Appl. No. 09/660,287, dated Nov. 13, 2000 (attached as Exhibit G to Amended Answer).
Information Disclosure Statement bearing, dated May 4, 2001 (attached as Exhibit F to Amended Answer).

(56) References Cited

OTHER PUBLICATIONS

Haas, N.P., et al., "Liss-Less Invasive Stabilization System—A New Internal Fixator for Distal Femur Fractures," OP J., vol. 13(3), pp. 340-344, Georg Thieme Verlag, Dec. 1997 (in English).
Gautier, E., et al., "Porosity and Remodelling of Plated Bone After Internal Fixation: Result of Stress Shielding of Vascular Damage?", Biomaterials and Biomechanics 1983, Elsevier Science Publishers B.V. 1984 ("Gautier").
Expert Report of John F. Witherspoon (w/o Exhibits A-C) in the Pennsylvania Action, dated Apr. 9, 2008; 36 pages.
Stryker, "VariAx Distal Radius: Locking Plate System", www.osteosynthesis.stryker.com, 2006, 12 pages.
International Patent Application No. PCT/US2008/072894: International Search Report dated Mar. 19, 2009, 18 pages.
European Patent Application No. 12006617.0: Extended European Search Report dated Jan. 21, 2013, 8 pages.
European Patent Application No. 12006615.4: Extended European Search Report dated Jan. 21, 2013, 7 pages.
European Patent Application No. 12006606.3: Extended European Search Report dated Jan. 21, 2013, 7 pages.
English translation of International Patent Application No. PCT/CH03/00577: International Search Report dated Apr. 28, 2004, 6 pages.
ACE Symmetry, "Curves in All the Right Places", 1996, 3 pages.
ACE Symmetry Trademark Titanium Upper Extremity Plates, ACE Medical Company, 1996, 2 pages.
"Multiple Offerings of Plates, Screws and Pegs", Small Bone Innovations, Inc., Dec. 2009, 3 pages.
"Cone Drive History and Double Enveloping Technology", http://conedrive.com/history/html, accessed Apr. 20, 2006, 9 pages.

\* cited by examiner

VARIABLE ANGLE BONE PLATE

CROSS-REFERENCE TO RELATED APPLICATIONS

This claims priority to U.S. Patent Application Ser. No. 62/385,107 filed on Sep. 8, 2016, the disclosure of which is hereby incorporated by reference as if set forth in its entirety herein.

BACKGROUND

This disclosure relates generally to bone fixation implants, and in particular relates to a bone plate that is configured to lockingly receive a bone screw at an angular orientation in a range of permissible angular orientations at which the bone plate can lockingly receive the bone screw.

When bones are damaged through trauma, disease, distraction osteogenesis, or orthognathic surgery, the defect is typically reduced, and bone fixation plates are commonly applied to the bone on opposite sides of the defect to ensure union in the desired position. Bone plates are typically made from a rigid material, such as titanium, and include fixation holes that are sized to be driven through the fixation holes and into the underlying bone to secure the bone plate to the bone. One common bone screw used in such application is generally referred to as a compression screw. Compression screws have unthreaded heads and threaded shafts. Accordingly, the compression screw can be driven through the fixation hole and into the underlying bone until the head applies a compression force against the bone plate toward the underlying bone. Another common bone screw used in such applications is generally referred to as a locking screw. Locking screws have threaded heads and threaded shafts. Accordingly, the locking screw can be driven through the fixation hole and into the underlying bone until the head threadedly mates with the bone plate in the fixation hole. Thus, the head of the locking screw does not apply a compressive force against the bone plate toward the underlying bone.

Conventionally, locking screws were inserted through the screw hole along the central screw hole axis in order to ensure that the threaded screw head mates with the bone plate in the threaded fixation hole. Recently, however, bone plates have been developed having threaded fixation holes that are configured to receive locking screws at different trajectories within a range of trajectories whereby the bone plate threadedly mates with the locking screw head in the threaded hole. While bone plates having such holes, commonly referred to as variable angle holes, have proved to be satisfactory for their intended purpose, improved variable angle holes are nevertheless desired.

SUMMARY

In accordance with one embodiment, a bone plate can include an inner surface configured to face bone, and an outer surface opposite the inner surface. The bone plate can further include an internal surface that extends from the outer surface to the inner surface, the internal surface defining a fixation hole that extends from the outer surface to the inner surface along a central hole axis and is sized to receive a shaft of a bone anchor that extends out with respect to a threaded head of the bone anchor along a central anchor axis. The internal surface can define 1) a tapered threaded region that includes a plurality of threaded columns that are circumferentially spaced from each other about the central hole axis and separated from each other by a corresponding plurality of recesses, and 2) a second region that extends between the tapered threaded region and the outer surface, the second region being concave as it extends along both a plane that includes the central hole axis, and a plane that is oriented perpendicular with respect to the central hole axis. The tapered threaded region can be configured to threadedly mate with the threaded head while the bone anchor is oriented at a first orientation with respect to the central hole axis. The tapered region can be further configured to threadedly mate with the threaded head when the bone anchor is oriented at a second orientation angle with respect to the central anchor axis that is different than the first orientation. The second region can be configured to receive a compression force from a compression screw that is inserted into the fixation hole such that a head of the compression screw abuts the second region.

BRIEF DESCRIPTION OF THE DRAWINGS

The foregoing summary, as well as the following detailed description, is better understood when read in conjunction with the appended drawings. For the purpose of illustrating the reconstruction device and related method thereof, there is shown in the drawings exemplary embodiments, in which like reference numerals correspond to like reference numerals throughout. The reconstruction device and related methods are not limited to the specific embodiments and methods disclosed, and reference is made to the claims for that purpose.

DETAILED DESCRIPTION

Figure 1:
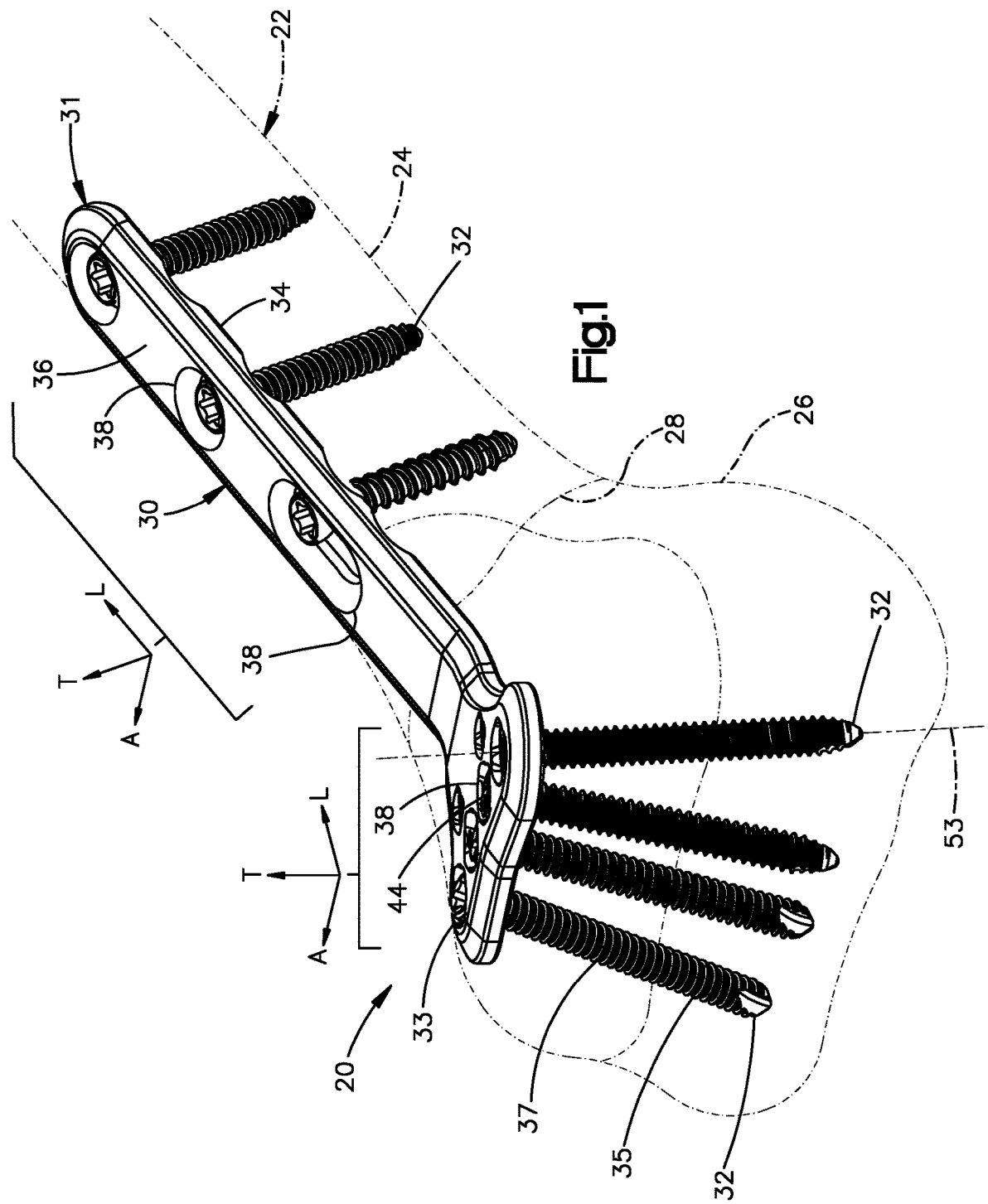
FIG. 1 is a perspective view of a bone fixation system constructed in accordance with one embodiment, including a bone plate and a plurality of fixation members that attach the bone plate to an underlying bone.

Referring initially to FIG. 1, a bone fixation system 20 is configured to be implanted onto bone 22 so as to stabilize a first bone segment 24 with respect to a second bone segment 26 that is separated from the first bone segment 24 by a defect 28. In one example, the first bone segment 24 can be defined by the diaphysis of the bone, while the second bone segment 26 can be defined by the metaphysis of the bone. It should be appreciated, however, that the first and second bone segments 24 and 26 can be defined by any region of the bone 22 as desired. Further, the bone 22 can be any bone in the human or animal anatomy suitable for bone plate fixation. Further still, while the bone 22 is illustrated having first and second bone segments 24 and 26, it is appreciated that the bone 22 can include any number of defects or bone fragments as desired that are configured for fixation using the bone fixation system 20. For instance, the diaphysis of the bone can include a plurality of bone fragments.

The bone fixation system 20 can include a bone plate 30 and a plurality of bone anchors 32 that are configured to fix the bone plate 30 to the underlying bone 22, and in particular to each of the first and second bone segments 22 and 24. The bone anchors 32 include a head 33 and a shaft 35 that extends out with respect to the head 33 along a central anchor axis 53. The shaft 35 can extend directly from the head, or can extend from a neck that is disposed between the head 33 and the shaft 35. The shaft 35 can be threaded, such that the bone anchor 32 is configured as a bone screw 37 whose shaft 35 extends out relative to the head 33 along the central anchor axis 53, which can also be referred to as a central screw axis. The threaded shaft 35 can be configured to threadedly purchase in the underlying bone 22. For instance, one or more up to all of the bone screw 37 can be configured as a cortical screw whose threaded shaft 35 is designed and configured to threadedly mate to cortical bone. Alternatively or additionally, one or more of the bone screws 37 can be configured as a cancellous screw whose threaded shaft 35 is designed and configured to threadedly mate to cancellous bone. It is appreciated that cancellous bone screws have threads that have a greater pitch than threads of cortical bone screws. Further, the threads of cancellous bone screws typically extend out from the shaft of the bone screw a greater distance than the threads of cortical bone screws.

The bone plate 30 defines a bone plate body 31. The bone plate body 31, and thus the bone plate 30, defines an inner surface 34 configured to face the underlying bone 22, and an outer surface 36 that is opposite the inner surface 34 along a transverse direction T. The bone plate 30 further defines a plurality of fixation holes 38 that extend through the bone plate body 31 from the inner surface 34 to the outer surface 36. In particular, the bone plate body 31, and thus the bone plate 30, includes a plurality of internal surfaces 39 that extend from the outer surface 36 to the inner surface 34 and defines a respective fixation hole 38 that extends from the outer surface 36 to the inner surface 34 along a central hole axis 45 (see FIGS. 7-8). The central hole axis 45 can be oriented along the transverse direction T. Thus, the central hole axis 45 can be oriented normal to each of the inner surface 34 and the outer surface 36. It should be appreciated, of course, that the central hole axis 45 can be oriented along any suitable direction with respect to the inner surface 34 and outer surface 36 as desired.

The fixation holes 38 are sized to receive the shaft 35 of a respective one of the bone screws 37. Thus, the bone screws 37 that extend through fixation holes 38 are permanent bone screws, meaning that they remain after completion of the surgical procedure. This is distinguished from temporary fixation holes that, for instance, can be configured to receive temporary fixation members, such as Kirschner wires that are removed prior to completion of the surgical procedure. In this regard, the fixation holes 38 can be referred to as permanent fixation holes. Accordingly, during operation, the shaft 35 of the bone screw 37 can be inserted through a respective one of the fixation holes 38 and into the underlying bone 22. The bone screw 37 can then be rotated so as to cause the threaded shaft 35 to be driven into the underlying bone as the threaded shaft 35 threadedly purchases with the underlying bone. The threaded shaft 35 can be driven into the underlying bone until the head 33 engages the bone plate 30. One or more up to all of the bone screws 37 can be configured as a compression screw whose head 33 is configured to bear against the bone plate 30 so as to apply a compressive force against the bone plate 30 toward the underlying bone 22 when the shaft 35 is driven further into the underlying after the head 33 has contacted the internal surface 39. The shaft 35 can be driven into the underlying bone a sufficient distance until the desired compressive force has been imparted onto the bone plate 30. The head 33 of the compression screw is often unthreaded. Similarly, at least a portion up to an entirety of the internal surface 39 can be unthreaded.

In another example, one or more up to all of the bone screw 37 can be configured as locking screws that are configured to lock to the bone plate 30. In particular, the head 33 can be externally threaded. The internal surface 39 can be similarly threaded so as to be configured to threadedly mate with the threaded head 33. Accordingly, during operation, the shaft 35 can be inserted through the fixation hole 38 and driven into the underlying bone as described above. In particular, when the bone screw 37 is a locking screw, rotation of the screw 37 causes the threaded head to threadedly mate with the internal surface 39. As a result, the screw head 33 fastens the bone plate 30 to the underlying bone without applying a compressive force onto the bone plate 30 against the underlying bone. The bone plate 30 can be spaced from the underlying bone when locked to the head 33. Alternatively, the bone plate 30 can abut the underlying bone when locked to the head 33. At least a portion of the internal surface 39 is typically tapered as it extends in an axially inward direction from the outer surface 36 toward the inner surface 34. Thus, the internal surface 39 is configured to prevent the head 33 from passing completely through the fixation hole 38. The head 33 can be constructed in accordance with any embodiment as described in U.S. Pat. No. 8,574,268, the disclosure of which is hereby incorporated by reference as if set forth in its entirety herein. Thus, it is appreciated that the head 33 can define at least one external thread that is circumferentially continuous about the central anchor axis 53. It should be appreciated, however, that the head 33 can be alternatively constructed in any manner desired so as to threadedly mate with the internal surface 39 as described herein.

Figure 3:
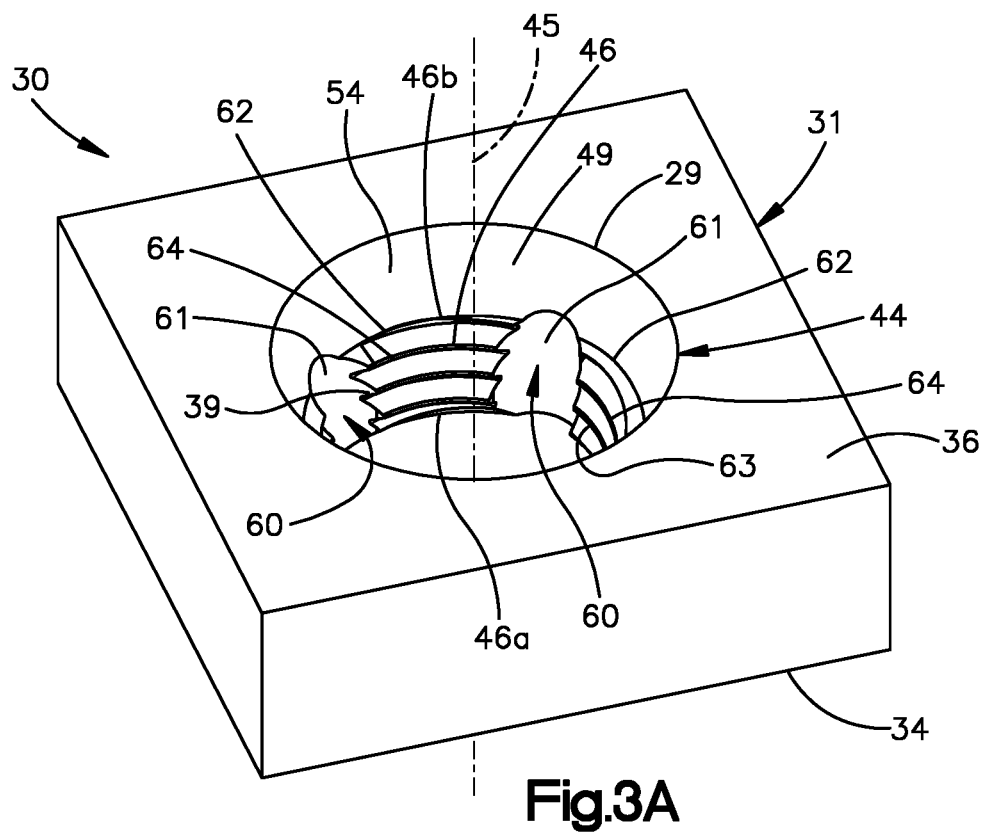
FIG. 3A is a perspective view of a portion of the bone plate illustrated in FIG. 1, showing a variable angle locking hole.
FIG. 3B is another perspective view of a portion of the bone plate illustrated in FIG. 3A.
Figure 4:
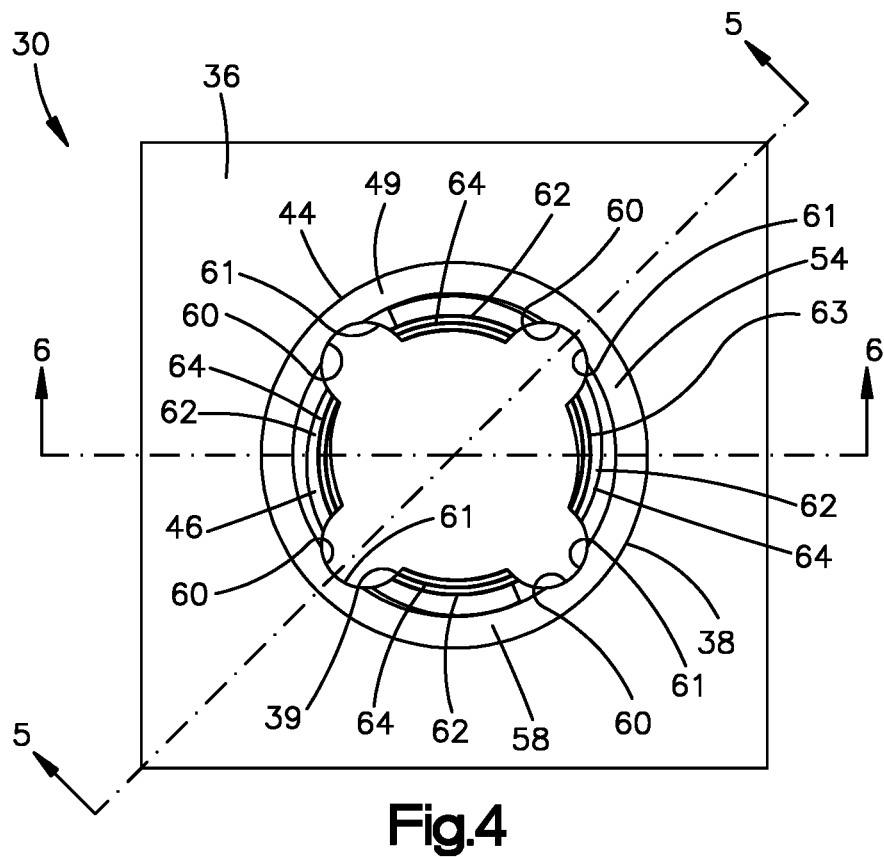
FIG. 4 is a top plan view of the portion of the bone plate illustrated in FIG. 3A.
Figure 5:
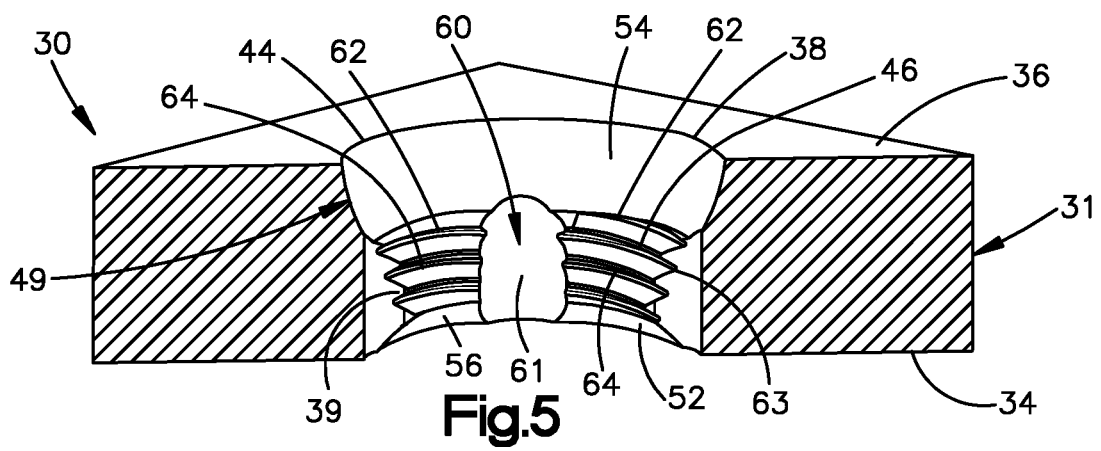
FIG. 5 is a sectional side elevation view of the portion of the bone plate illustrated in FIG. 4, taken along line 5-5.
Figure 6:
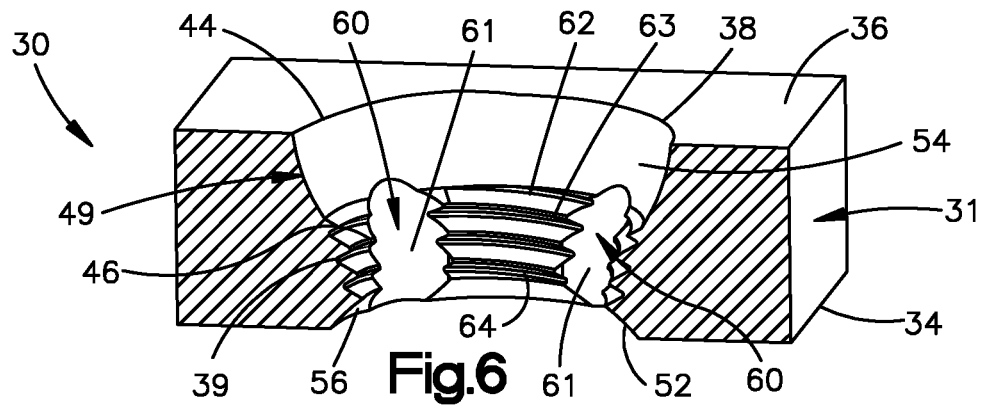
FIG. 6 is a sectional side elevation view of the portion of the bone plate illustrated in FIG. 4, taken along line 6-6.

Referring now to FIGS. 1 and 3A-3B, at least one of the fixation holes 38 of the bone plate 30 is configured as a variable angle locking hole 44 that is configured to threadedly mate with the bone screw 37 at different orientations of the bone screw 37 with respect to the central hole axis 45. That is, when the fixation hole 38 is configured as a variable angle locking hole 44, the bone plate body 31, and thus the bone plate 30, includes at least one thread 46 that projects out from the internal surface 39 into the fixation hole 38.

The bone screw 37 is configured to be inserted into the fixation hole 38 such that the central anchor axis 53 is at one of a plurality of orientations with respect to the central hole axis 45 within a range of orientations at which the threaded head 33 is configured to threadedly mate with the at least one thread 46 in the fixation hole 38. For instance, the bone screw 37 is configured to be inserted into the fixation hole 38 such that the central anchor axis 53 is at one of a plurality of angles within a range of angles defined by the central anchor axis 53 and the central hole axis 45 at which the threaded head 33 is configured to threadedly mate with the at least one thread 46 in the fixation hole 38. The range of angles can be from approximately zero degrees to approximately 15 degrees. Thus, the range of angles can define a cone of up to thirty degrees. Thus, it can be said that the at least one thread 46 is configured to threadedly mate with the threaded screw head 33 while the bone screw 37 is inserted into the fixation hole 38 such that the central anchor axis 53 is oriented at a first angle with respect to the central hole axis 45, and the at least one thread 46 is further configured to threadedly mate with the threaded screw head 33 when the bone screw 37 is inserted into the fixation hole 38 such that the central anchor axis 53 is oriented at a second angle with respect to the central hole axis 45 that is different than the first angle. At least one or both of the first and second angles can be non-zero angles. Alternatively, the central anchor axis 53 can be coincident with the central hole axis 45 in one of the orientations in the range of orientations. The threads 46 and the threads of the head 33 are defined prior to insertion of the bone screw 37 into the variable angle locking hole 44. That is, the internal surface 39 is not designed or configured to cut threads into the bone screw head 33. Similarly, the bone screw head 33 is not designed or configured to cut threads into the internal surface 39. The variable angle locking hole 44 is described in more detail below.

Figure 2:
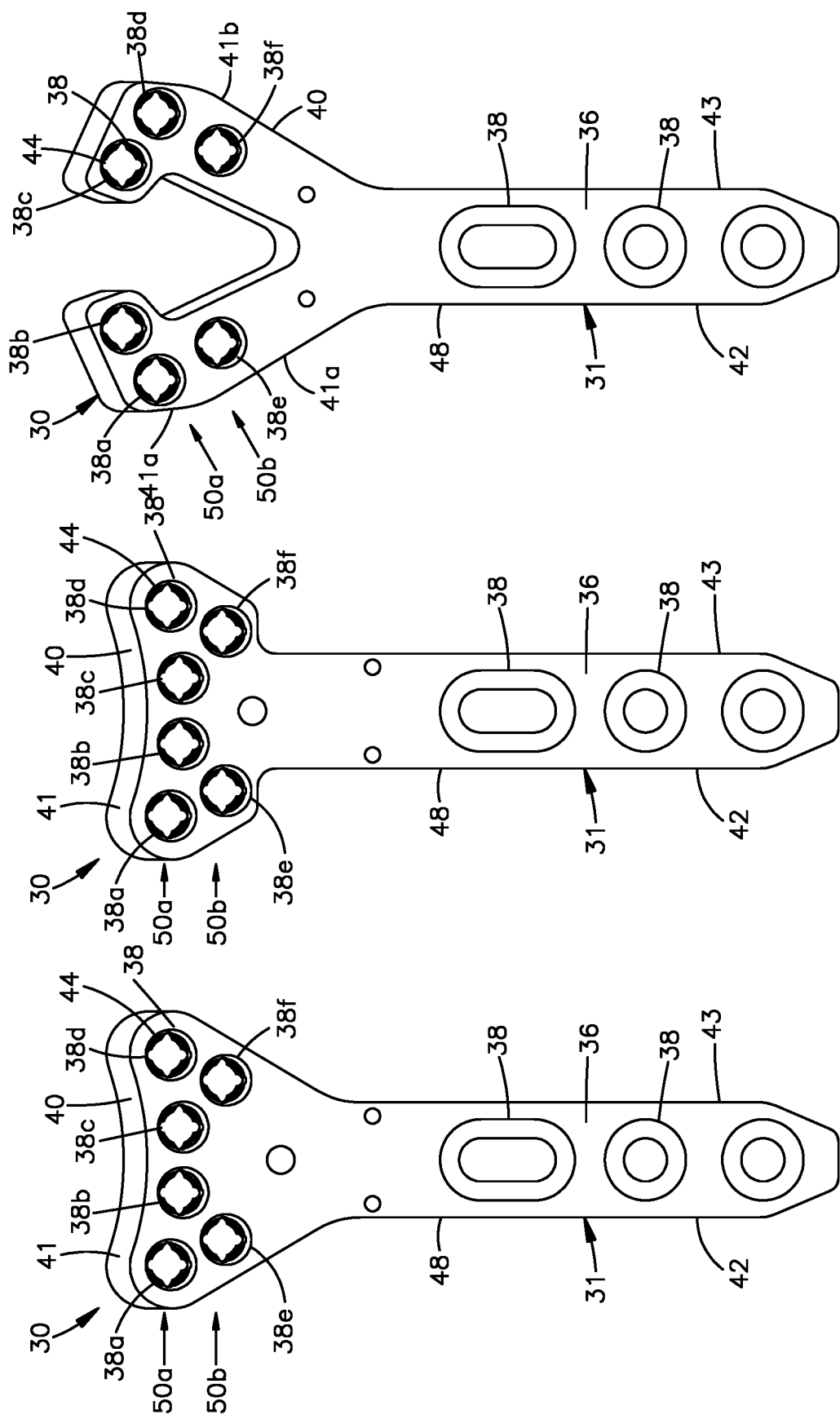
FIG. 2A is a perspective view of the bone plate illustrated in FIG. 1, constructed in accordance with one embodiment.
FIG. 2B is a perspective view of a bone plate constructed in accordance with another embodiment.
FIG. 2C is a perspective view of a bone plate constructed in accordance with yet one embodiment.

Referring now to FIGS. 2A-2C, the bone plate 30 can be configured in any suitable manner as desired. In one example, the bone plate body 31, and thus the bone plate 30, can include a first plate portion 40 and a second plate portion 42. In one example, the first plate portion 40 can define a plate head portion 41 that is configured to overlie the second bone segment 26, and the second plate portion 42 can be referred to as a plate shaft portion 43 that is configured to overlie the first bone segment 24. Each of the plate head portion 41 and the plate shat portion 43 can include at least one up to a plurality of bone fixation holes 38. Thus, bone anchors 32 that extend through respective fixation holes 38 of the plate head portion 41 can be driven into the metaphysis region of the underlying bone, and bone anchors 32 that extend through respective fixation holes 38 of the plate shaft portion 43 can be driven into the diaphysis region of the underlying bone. The metaphysis region can, for instance, be defined by the distal region of the radius bone. Any one or more up to all of the fixation holes 38 of the bone plate 30 can be compression holes, locking holes, or variable angle locking holes 44.

In one example, all of the fixation holes 38 in the first plate portion 40 are variable angle locking holes 44. Further, in one example, all of the fixation holes 38 in the second plate portion 42 are compression holes configured to receive cortical bone screws. Further, at least one or more up to all of the compression holes can be configured as slots that are elongate along a central longitudinal axis of the bone plate to allow for positional flexibility of the bone screw received therein. Alternatively or additionally, at least one or more up to all of the compression holes can have a circular cross-section so as to locate the position of the bone screw received therein. As described above, however, it should be appreciated that the bone plate 30 can be configured to attach to any region or regions of any suitable bone in the human or animal anatomy suitable for bone plate fixation.

Referring to FIGS. 2A-2C, the bone plate 30 is illustrated in accordance with three non-limiting examples. In FIGS. 2A-2C, the bone plate 30 defines a length that extends along a longitudinal direction L, a width that is less than the length and extends along a lateral direction A that is perpendicular to the longitudinal direction L, and a thickness that is less than both the length and the width and extends along the transverse direction T that is perpendicular to each of the longitudinal direction L and the lateral direction A. The bone plate 30 defines a distal direction from the plate shaft portion 43 to the plate head portion 41, and a proximal direction from the plate head portion 41 to the plate shaft portion 43. The distal and proximal directions can be oriented along the longitudinal direction L. The bone plate 30 illustrated in FIGS. 2A-2C has an outer perimeter 48 that is defined by the plate shaft potion 43 and the plate head portion 41. Further, at least a portion of the plate head portion 41 of the bone plate 30 illustrated in FIGS. 2A-2C can be angled so as to extend outward as it extends in the distal direction away from the plate shaft portion 43.

Referring now to FIG. 2A in particular, the outer perimeter 48 can be substantially Y-shaped. That is, the outer perimeter 48 can flare away outward as it extends along the distal direction from the plate shaft portion 43. Thus, the width of the bone plate 30 at the plate head portion 41 increases as it extends in the distal direction. The width can increase at a constant rate. Alternatively, the width can increase at an increasing rate. Alternatively still, the width can increase at a decreasing rate. The plate head portion 41 can define a plurality of fixation holes 38. One or more up to all of the fixation apertures in the plate head portion 41 can be configured as variable angle locking holes 44.

The fixation holes 38 of the head portion 41 can be arranged in a first row 50a and a second row 50b that is offset from the first row 50a in the proximal direction. The first row 50a can contain a greater number of fixation holes 38 than the second row 50b. For instance, the first row 50a can contain double the number of fixation apertures of the second row 50b. In one example, the first row 50a can include four fixation holes 38, with first and second ones 38a and 38b of the fixation holes 38 of the first row 50a disposed on a first side of a longitudinal centerline of the bone plate 30, and third and fourth ones 38c and 38d of the fixation holes 38 of the first row 50a disposed on a second side of the longitudinal centerline of the bone plate 30 opposite the first side. The first one 38a of the fixation holes 38 of the first row 50a can be disposed laterally outward with respect to the second one 38b of the fixation holes 38 of the first row 50a. Similarly, the third one 38c of the fixation holes 38 of the first row 50a can be disposed laterally outward with respect to the fourth one 38d of the fixation holes 38 of the first row 50a. Further still, the central hole axis of the fourth one 38d of the fixation holes 38 of the first row 50a can be offset from the central hole axis of all other ones of the fixation holes 38 of the first row 50a in the distal direction. It should be appreciated, of course, that the first row 50a can include any number of fixation holes 38 as desired, arranged as desired. Further, the first and second rows 50a and 50b can be linear rows or can be curved as desired. In one example, the central hole axes of the fixation holes 38 of the fixed row lie on a nonlinear path.

The second row 50b can include likewise include any number of fixation holes 38 as desired. In one example, the second row 50b can include first and second ones 38e and 38f, respectively, of the fixation holes 38. The central hole axes of the fixation holes 38 of the second row 50b are spaced from the central hole axes of the fixation holes 38 of the first row 50a in the proximal direction. The first one 38e of the fixation holes 38 of the second row 50b can be disposed between the first and second ones 38*a* and 38*b* of the fixation holes 38 of the first row 50*a* with respect to the lateral direction A. Similarly, the second one 38*f* of the fixation holes 38 of the second row 50*b* can be disposed between the third and fourth ones 38*c* and 38*d* of the fixation holes 38 of the first row 50*a* with respect to the lateral direction A.

The first and second ones 38*a* and 38*b* of the fixation holes 38 of the first row 50*a* and the first one 38*e* of the fixation holes 38 of the second row 50*b* can be configured to receive bone screws that are driven into one of the lunate fossa and the sigmoid notch. The third one 38*c* of the fixation holes 38 of the first row 50*a* can be configured to receive a bone screw that is driven into the scaphoid fossa. The fourth one 38*d* of the fixation holes 38 of the first row 50*a* and the second one 38*f* of the fixation holes 38 of the second row 50*b* can be configured to receive bone screws that are driven into one of the styloid process. It is recognized that the central hole axes 45 of one or more up to all of the fixation holes 38*a*-38*f* can be perpendicular to one or both of the bone plate surfaces 34 and 36, or nonperpendicular to one or both of the bone plate surfaces 34 and 36. In one example, the respective central hole axes 45 of the fixation holes 38*d* and 38*f* may define an angle with respect to one or both of the bone plate surfaces 34 and 36 that is less than the angle defined by the central hole axes of the other fixation holes 38*a*-38*c* and 38*e* and the one or both of the bone plate surfaces 34 and 36. Thus, the bone fixation holes 38*d* and 38*f* can be said to have increased angulation with respect to the other fixation holes 38*a*-38*c* and 38*e*. The increased angulation can allow bone screws that are inserted through the fixation holes 38*d* and 38*f* to be aligned with the styloid reach for fixation to the styloid reach.

Referring now to FIG. 2B in particular, the outer perimeter 48 can be substantially T-shaped. That is, the outer perimeter 48 can define opposed shoulders that flare out from the plate shaft portion 43 along the lateral direction A so as to define a proximal-most aspect of the plate head portion 41. The outer perimeter 48 can flare outward along the lateral direction A as it extends in the distal direction from the shoulders. Thus, the width of the bone plate 30 at the plate head portion 41 increases as it extends in the distal direction. The width can increase at a constant rate. Alternatively, the width can increase at an increasing rate. Alternatively still, the width can increase at a decreasing rate. The plate head portion 41 can define a plurality of fixation holes 38. One or more up to all of the fixation apertures in the plate head portion 41 can be configured as variable angle locking holes 44.

The fixation holes 38 of the head portion 41 can be arranged in a first row 50*a* and a second row 50*b* that is offset from the first row 50*a* in the proximal direction. The first row 50*a* can contain a greater number of fixation holes 38 than the second row 50*b*. For instance, the first row 50*a* can contain double the number of fixation apertures of the second row 50*b*. In one example, the first row 50*a* can include four fixation holes 38, with first and second ones 38*a* and 38*b* of the fixation holes 38 of the first row 50*a* disposed on a first side of a longitudinal centerline of the bone plate 30, and third and fourth ones 38*c* and 38*d* of the fixation holes 38 of the first row 50*a* disposed on a second side of the longitudinal centerline of the bone plate 30 opposite the first side. The first one 38*a* of the fixation holes 38 of the first row 50*a* can be disposed laterally outward with respect to the second one 38*b* of the fixation holes 38 of the first row 50*a*. Similarly, the third one 38*c* of the fixation holes 38 of the first row 50*a* can be disposed laterally outward with respect to the fourth one 38*d* of the fixation holes 38 of the first row 50*a*. Further still, the central hole axis of the fourth one 38*d* of the fixation holes 38 of the first row 50*a* can be offset from the central hole axis of all other ones of the fixation holes 38 of the first row 50*a* in the distal direction. It should be appreciated, of course, that the first row 50*a* can include any number of fixation holes 38 as desired, arranged as desired. Further, the first and second rows 50*a* and 50*b* can be linear rows or can be curved as desired. In one example, the central hole axes of the fixation holes 38 of the fixed row lie on a nonlinear path.

The second row 50*b* can include likewise include any number of fixation holes 38 as desired. In one example, the second row 50*b* can include first and second ones 38*e* and 38*f*, respectively, of the fixation holes 38. The central hole axes of the fixation holes 38 of the second row 50*b* are spaced from the central hole axes of the fixation holes 38 of the first row 50*a* in the proximal direction. The first one 38*e* of the fixation holes 38 of the second row 50*b* can be disposed between the first and second ones 38*a* and 38*b* of the fixation holes 38 of the first row 50*a* with respect to the lateral direction A. Similarly, the second one 38*f* of the fixation holes 38 of the second row 50*b* can be disposed between the third and fourth ones 38*c* and 38*d* of the fixation holes 38 of the first row 50*a* with respect to the lateral direction A.

The first and second ones 38*a* and 38*b* of the fixation holes 38 of the first row 50*a* and the first one 38*e* of the fixation holes 38 of the second row 50*b* can be configured to receive bone screws that are driven into one of the lunate fossa and the sigmoid notch. The third one 38*c* of the fixation holes 38 of the first row 50*a* can be configured to receive a bone screw that is driven into the scaphoid fossa. The fourth one 38*d* of the fixation holes 38 of the first row 50*a* and the second one 38*f* of the fixation holes 38 of the second row 50*b* can be configured to receive bone screws that are driven into one of the styloid process. As described above with respect to FIG. 2A, it is recognized that the central hole axes 45 of one or more up to all of the fixation holes 38*a*-38*f* can be perpendicular to one or both of the bone plate surfaces 34 and 36, or nonperpendicular to one or both of the bone plate surfaces 34 and 36. In one example, the respective central hole axes 45 of the fixation holes 38*d* and 38*f* may define an angle with respect to one or both of the bone plate surfaces 34 and 36 that is less than the angle defined by the central hole axes of the other fixation holes 38*a*-38*c* and 38*e* and the one or both of the bone plate surfaces 34 and 36. Thus, the bone fixation holes 38*d* and 38*f* can be said to have increased angulation with respect to the other fixation holes 38*a*-38*c* and 38*e*. The increased angulation can allow bone screws that are inserted through the fixation holes 38*d* and 38*f* to be aligned with the styloid reach for fixation to the styloid reach.

Referring now to FIG. 2C in particular, the outer perimeter 48 can be forked. That is, the plate head portion 41 can define first and second arms 41*a* and 41*b* that extend away from the plate shaft portion 43 in the distal direction, and are spaced from each other along the lateral direction A. Respective first portions of the first and second arms 41*a* and 41*b* can flare away from each other along the lateral direction A as they extend away from the plate shaft portion 43. Thus, the laterally outer perimeter 48 at the first portion of the plate head portion 41 can flare out along the lateral direction A as it extends in the distal direction. Respective second portions of the first and second arms 41*a* and 41*b* can flare toward from each other along the lateral direction A as they extend away from the respective first portions. Thus, the laterally outer perimeter 48 at the second portion of the plate head portion 41 can flare in along the lateral direction A as it extends in the distal direction. The arms 41a and 41b can be disposed on opposite sides of the longitudinal centerline of the plate 30.

Each of the first and second arms 41a and 41b can include at least one fixation hole 38 such as a plurality of fixation holes 38. One or more up to all of the fixation apertures in the plate head portion 41 can be configured as variable angle locking holes 44. The fixation holes 38 of each of the arms 41a and 41b can be arranged in a respective first row 50a and a second row 50b that is offset from the first row 50a in the proximal direction. The first row 50a can be oriented substantially parallel to the outer perimeter 48 at the distal-most end of the respective arms 41a and 41b. For instance, the first row 50a can contain double the number of fixation apertures of the second row 50b. In one example, the first row 50a can include first and second ones 38a and 38b of the fixation holes 38 of the first and second arms 41a and 41b, respectively. It should be appreciated, of course, that the first row 50a can include any number of fixation holes 38 as desired, arranged as desired.

The second row 50b of each of the first and second arms 41a and 41b can include likewise include any number of fixation holes 38 as desired. In one example, the second row 50b can include a respective one 38c of the fixation holes 38. The central hole axes of the fixation hole 38 of the second row 50b are spaced from the central hole axes of the fixation holes 38 of the first row 50a in the proximal direction. The respective one 38c of the fixation holes 38 of the second row 50b can be disposed between the first and second ones 38a and 38b of the fixation holes 38 of the first row 50a with respect to the lateral direction A.

The first and second ones 38a and 38b of the fixation holes 38 of the first rows 50a can be configured to receive bone screws that are driven into the lunate fossa and sigmoid notch. Bone screws inserted into the hole 38c can be aligned to be driven into the scaphoid fossa. Bone screws inserted into the hole 38d can be aligned to be driven into a styloid fragment. The fixation hole 38 of the second row 50b can be configured to receive a bone screw that is driven into the lunate fossa and sigmoid notch. Bone screws can be driven into hole 38f of the second row to reach and support a styloid fragment.

The variable angle locking hole 44 will now be described, with initial reference to FIGS. 3A-6. In particular, and as described above, the bone plate 30 can include at least one up to a plurality of variable angle locking holes 44. One of the locking holes 44 will now be described in detail, it being that the description is applicable to the other locking holes of the bone plate 30. The bone plate 30 includes the internal surface 39 that extends from the inner surface 34 to the outer surface 36. The internal surface 39 defines the fixation hole 38 that similarly extends through the bone plate body 31 from the outer surface to the inner surface along the central hole axis 45. In one example, the central hole axis 45 can extend along the transverse direction T. It should be appreciated, of course, that the central hole axis 45 can be oriented along any direction as desired, including a direction that is angularly offset with respect to the transverse direction T. As described above, the inner and outer surfaces 34 and 36 are opposite each other along the transverse direction T. Thus, in some examples, the transverse direction T defined by the head portion 41 of the bone plate 30 may be angularly offset with respect to the transverse direction T defined by the shaft portion 43 of the bone plate 30. In other examples, the transverse direction T can be constant along an entirety of the length of the bone plate 30.

The fixation hole 38 is sized to receive the shaft 35 of the bone anchor 32. In particular, the fixation hole 38 has a cross-sectional dimension that is defined from one location of the internal surface 39 to another radially opposite location of the internal surface 39 along a straight linear direction that passes through the central hole axis 45 and is perpendicular to the central hole axis 45. In one example, the cross-sectional dimension defines a diameter of the internal surface 39. Thus, the internal surface 39 can extend along a circular path in cross-section along a plane that is oriented normal to the central hole axis 45. However, it is recognized that the internal surface 39 can define any suitable geometry as desired. The cross-sectional dimension is greater than the outer diameter of the at least one thread of the bone anchor shaft 35, such that the shaft 35 can travel through the variable angle locking hole 44 so as to extend out from the inner surface 34 and into the underlying bone.

The variable angle locking hole 44 can include the at least one thread 46 that is configured to threadedly mate with the threaded head 33 of the bone anchor 32. In particular, the at least one thread 46 can extend from at least a portion of the internal surface 39 into the fixation hole 38. In one example, the thread 46 can be monolithic with the internal surface 39. Because the at least one thread 46 is an internal at least one thread 46, the at least one thread 46 defines a major diameter at the interface between the at least one thread 46 and the internal surface 39. The at least one thread 46 can extend out from the internal surface to a minor diameter that is radially inwardly spaced from the major diameter. The minor diameter can be sized greater than the outer diameter of the at least one thread of the bone anchor shaft 35, such that the shaft 35 can travel through the variable angle locking hole 44 so as to extend out from the inner surface 34 and into the underlying bone. The radially inward direction, as used herein, can be defined as a direction toward the central hole axis 45. A radially outward direction is opposite the radially inward direction. Thus, the radially outward direction, as used herein, can be defined as a direction away from the central hole axis 45. A direction normal to the central hole axis 45 can be said to be radial direction.

In one embodiment, the at least one thread 46 extends along a portion of the axial length of the internal surface 39. Alternatively, the at least one thread 46 can extend along an entirety of the axial length of the internal surface 39. The at least one thread 46 can define a thread path that is sloped with respect to a reference plane. The reference plane can be normal to the central hole axis 45. Thus, the reference plane can be defined by the radial direction. The thread path can be defined by the minor diameter of the at least one thread 46 that defines the thread crest. In one example, the at least one thread 46 can be a helical thread. Thus, the thread path can define a helix. Further, the at least one thread 46 can define a single thread. Alternatively, the at least one thread 46 can include multiple threads. For instance, the at least one thread 46 can be configured as a double lead thread or alternative multiple lead thread.

The internal surface 39 defines an axially inner end 52 that can extend to the inner surface 34. The axially inner end 52 can define an edge that is shared by the inner surface 34. Alternatively, the axially inner end 52 can flare radially outward as it extends in the axially inward direction toward the inner surface 34. In one example, the axially inner end 52 flares radially outward as it extends in the axially inward direction. The axially inner end of the internal surface 39 can be defined by an undercut 56 that flares radially outward to the axially inner surface 34. For instance, the undercut 56 can flare linearly to the axially inner surface 34. Alternatively, at least a portion up to all of the undercut 56 can be curved as it extends to the axially inner surface 34. The undercut 56 can extend about an entirety of the perimeter of the variable angle locking hole 44. Further, the axially outer end of the undercut 56 can be defined by an edge that is defined by a radius of between approximately 0.75 mm and approximately 1.75 mm, such as between approximately 1 mm and approximately 1.5 mm, for instance approximately 1.4 mm. The edge can be interrupted by recesses 60 as described in more detail below.

The at least one thread 46 can extend radially inward from the inner surface 34 at the undercut 56. Alternatively, the undercut 56 can be devoid of threads, and can be substantially smooth. As will be appreciated from the description below, the undercut 56 can cause the internal surface 39 to avoid contact with the shaft 35 at angles between the central anchor axis 53 and the central hole axis 45 that would be prevented due to contact between the internal surface 39 and the shaft 35 without the undercut 56. Thus, the undercut 56 can widen the range of angles that are defined by the central anchor axis 53 and the central hole axis 45 at which the threaded head 33 is configured to threadedly mate with the at least one thread 46 in the fixation hole 38.

The internal surface 39 defines an axially outer end 54 that is opposite the axially inner end 52. The axially outer end 54 can extend to the outer surface 36. The axially outer end 54 can define an edge that is shared by the inner surface 34. As is described in more detail below, the axially outer end 54 can be defined by a second region 49 of the internal surface 39. The second region can be unthreaded. The second region 49 of the internal surface 39 can be concave with respect to a view in the radially outward direction from the central hole axis 45. The fixation hole 38 can be configured to receive the head of a compression screw, such that the head of the compression screw abuts the second region 49 and applies a compression force to the bone plate that urges the bone plate toward, for instance against, the underlying bone as the compression screw is driven into the underlying bone. It should be appreciated that the axially inward and axially outward directions can be oriented along the transverse direction T, or can define an angle with respect to the transverse direction T. For instance, the internal surface 39 can be tapered and extend along the axial direction that includes both the axially inward direction and the axially outward direction.

The at least one thread 46 can extend from a first location 46a to a second location 46b that is offset from the first location 46a along the axially outward direction. The at least one thread terminates at the first location 46a and the second location 46b. The first location 46a can extend to the inner end 52 of the internal surface 39. Thus, the first location 46a can extend to the inner surface 34. Alternatively, the first location 46a can be offset from the inner surface 34 along the axially outward direction. The second location 46a can extend to the outer end 54 of the internal surface 39. Thus, the first location 46a can extend to the second region 49 of the internal surface 39. Alternatively, the second location 46b can extend to the outer surface 36. Alternatively, the second location 46b can be offset from the outer surface 36 along the axially inward direction.

Figure 9A:
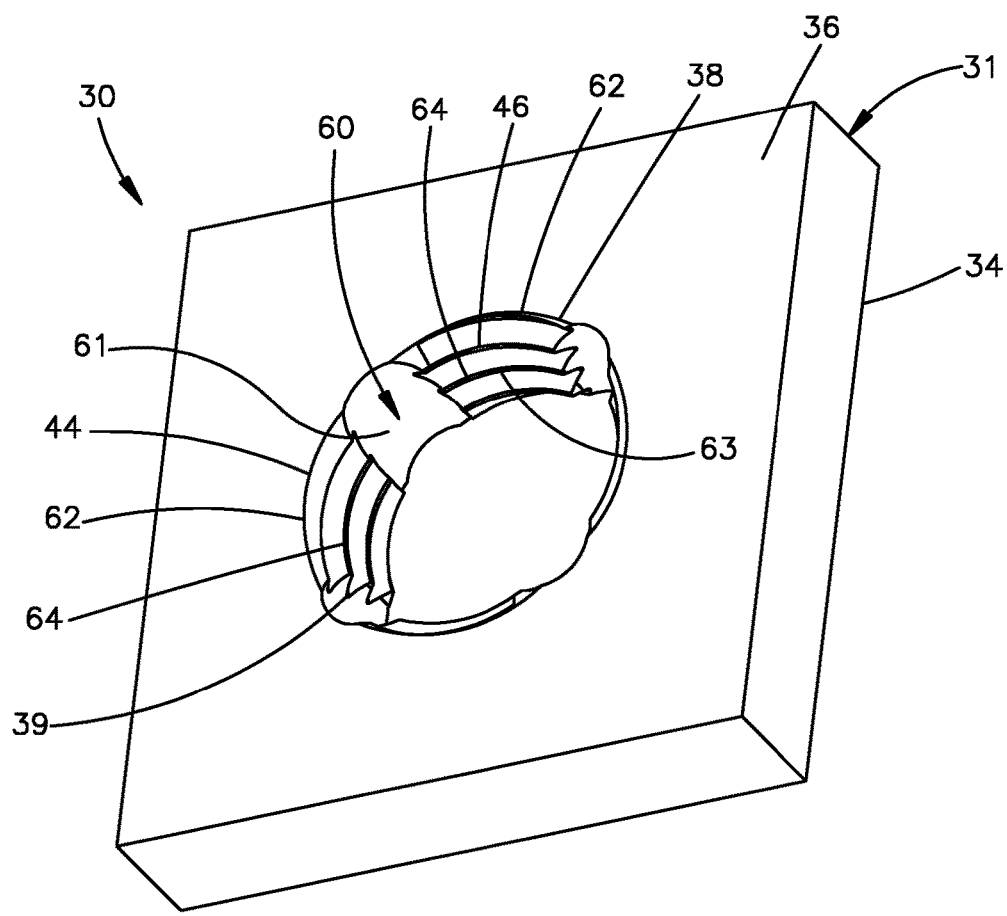
FIG. 9A is a perspective view of the portion of the bone plate illustrated in FIG. 4, but shown in accordance with an alternative embodiment.
Figure 9B:
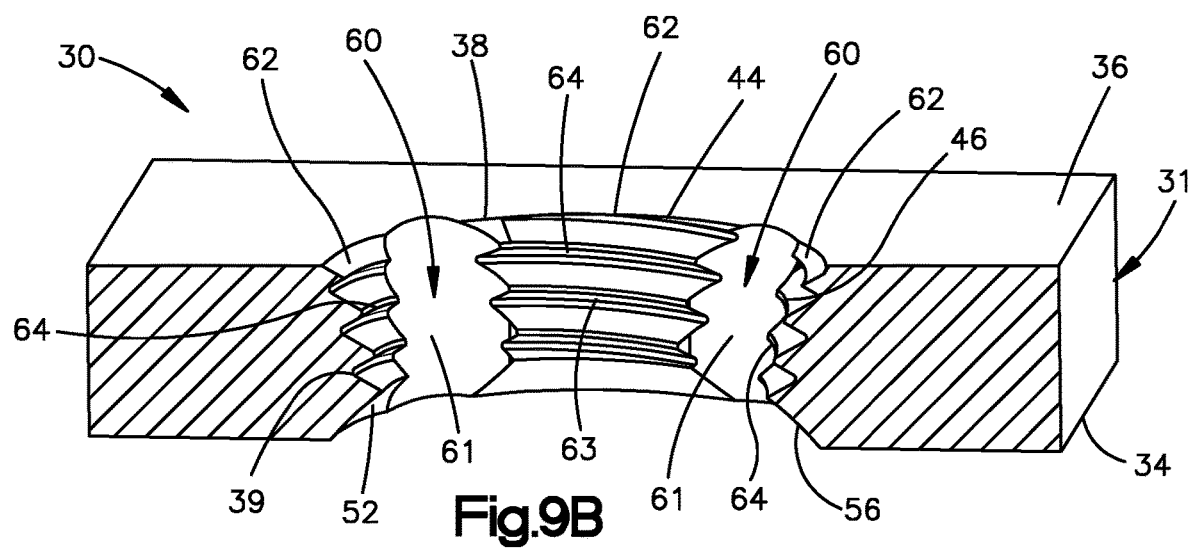
FIG. 9B is a sectional perspective view of the portion of the bone plate illustrated in FIG. 9A.

With continuing reference to FIGS. 3A-6, the plate body 31, and thus the bone plate 30, can define a plurality of (e.g., at least two) recesses 60 that divide the at least one thread 46 into a plurality of (e.g., at least two) columns 62. In particular, the recesses 60 divide the at least one thread 46 into a plurality of columns 62 of thread segments 64 that are described in more detail below. Each of the columns 62 can extend from an axially outer end of the respective column to an axially inner end of the respective column. The axially outer end of the columns 62 can terminate at the second region 49. Alternatively, as illustrated in FIGS. 9A-9B, the axially outer end of the columns 62 can terminate at the outer surface 36. The axially inner end of the columns 62 can terminate at the undercut 56. Alternatively, the axially inner end of the columns 62 can terminate at the axially inner surface 34. For instance, the at least one thread 46 can extend along the undercut 56, and the recesses 60 can extend into the undercut 56, such that the axially inner ends of the columns 62 extend to the axially inner surface 34. Alternatively, the at least one thread 46 can terminate without extending along the undercut 56, and the recesses 60 can extend into the undercut 56, such that the axially inner ends of the columns 62 extend to the axially inner surface 34. Alternatively still, the bone plate can be devoid of the undercut 56, such that the axially inner ends of the columns 62 extend to the axially inner surface 34.

Opposed pairs of the columns 62 can be disposed radially opposite each other through the central hole axis 45. At least a portion up to an entirety of each of the recesses 60 can extend through the threaded region 47 at least to the internal surface 39 along the radially outward direction away from the central hole axis 45. For instance, at least a portion up to an entirety of each of the recesses can extend into the internal surface 39 along the radially outward direction away from the central hole axis 45. Thus, at least a portion up to an entirety of the recesses 60 can further extend radially outward through the at least one thread 46 that is carried by the internal surface 39. Each of the recesses 60 terminates radially at a respective recessed surface 61 of the plate body 31. Thus, it can be said that the recesses 60 can be at least partially or fully defined by the recessed surface 61. It can further be said that each recessed surface 61 defines a radial outer perimeter of the respective recesses 60. The recesses 60 can extend through the bone plate body 31 from the axially inner surface 34 to the axially outer surface 36. The recessed surface 61 of each of the recesses 60 between adjacent ones of the columns 62 can define any suitable surface area as desired. For instance, the surface area of the recessed surface 61 of each of the recesses 60 from the inner surface 34 to the outer surface 36 can be between approximately $3^2$ mm and approximately 5 mm$^2$, such as between approximately 4 mm$^2$ and approximately 4.5 mm$^2$, such as approximately 4.4 mm$^2$. The terms "approximate" and "substantially" as used herein with respect to dimensions and shapes recognizes that manufacturing tolerances along with other factors, such as rounding, can cause variation in measurements and distances. Further, term "between" with respect to ranges of dimensions is used herein to also include the respective dimensions.

In one example, the plate body 31 can include four recesses 60 that are circumferentially spaced apart from each other. However, it is appreciated that the plate body 31 can include any number of recesses 60, greater than one, as desired, so as to define the variable angle locking hole 44 of the type described herein. Further, the circumferential distance of the recessed surfaces of each of the recesses 60 can be the same as each other along a common plane that is oriented normal to the central hole axis 45. In this regard, each of the recesses 60 can be sized and shaped substantially identical to each other. Further, the recesses 60 can be circumferentially equidistantly spaced from each other about the central hole axis 45. Alternatively, the recesses 60 can be circumferentially spaced from each other a variable distance about the central hole axis 45. Similarly, the plate body 31 can include four columns 62 of thread segments 64 that are circumferentially spaced apart from each other. However, it is appreciated that the plate body 31 can include any number of columns 62, greater than one, as desired, so as to define the variable angle locking hole 44 of the type described herein. The columns 62 can be sized and shaped substantially identical to each other. Further, the columns 62 can be circumferentially equidistantly spaced from each other about the central hole axis 45. Alternatively, the columns 62 can be circumferentially spaced from each other a variable distance about the central hole axis 45.

The recesses 60 can have a radial depth sufficient such that the recessed surface 61 is recessed with respect to the internal surface 39 along the radially outward direction. That is, the recessed surface 61 can define a radial distance from the central hole axis 45 that is greater than the radial distance from the central hole axis 45 to the major diameter of the at least one thread 46. Further, an entirety of the recessed surface 61 can define a curvature along a plane that is oriented normal to the central hole axis 45 from a first end of the recessed surface 61 that adjoins the internal surface 39 of one of the columns 62 to a second end of the recessed surface 61 that adjoins the internal surface 39 at another one of the columns 62. The curvature can be a constant curvature from the first end to the second end. In one example, the recessed surface 61 extends along a circular path along the plane that is oriented normal to the central hole axis 45.

The recesses 60 further extend in the axially outer direction defined from the axially inner surface 34 toward the outer surface 36. In one example, each of the recesses 60 can extend from a respective axially first or inner terminal end to a respective opposed axially second or outer terminal end. The inner terminal end can be disposed at the axially inner surface 34. Alternatively or additionally, depending on the size of the undercut 56, the inner terminal end can extend into the undercut 56. Alternatively still, the inner terminal end of the recesses 60 can be circumferentially aligned with the inner terminal end of the columns 62. The undercut 56 can be localized at a location aligned with the columns 62 so as to not extend circumferentially beyond the column 62. Alternatively, the undercut 56 can extend about the entire perimeter of the variable angle locking hole 44. The outer terminal ends of the recesses 60 can be spaced axially inward from the axially outer surface 36. Alternatively, as illustrated in FIGS. 9A-9B, the outer terminal ends 60 can extend to the axially outer surface 36.

The axially outer surface 36 can define an opening 29 of the variable angle locking hole 44. The opening 29 thus has an outer perimeter that is defined by the axially outer surface 36 of the bone plate 30. The axially outer surface 36 at the opening 29 can be defined entirely by the internal surface 39. The recessed surfaces 61 of each of the recesses 60, in their respective entireties, can be offset from the outer perimeter of the opening 29 in the radially inward direction, that is toward the central hole axis 45. Thus, the axially outer surface 36 at the opening 29 can define a circle. It should be appreciated, of course, that the axially outer surface 36 at the opening 29 can define any suitable alternative shape as desired. For instance, as illustrated in FIG. 9A-9B, the recesses 60 can extend through the bone plate body to the axially outer surface 36, such that the recessed surfaces partially define the outer perimeter. Thus, the axially outer surface 36 at the opening 29 can be defined by both the internal surface 39 and the recessed surfaces 61. The axially outer surface 36 at the opening 29 at locations defined by the internal surface 39 can be concave to the central hole axis 45 and defined by a first curvature, and the axially outer surface 36 at the opening 29 at locations defined by the recessed surfaces 61 can be concave to the central hole axis 45 and defined by a second curvature that is greater than the first curvature.

Adjacent ones of the columns 62 can be separated by a common one of the recesses 60. The adjacent ones of the columns 62 can be referred to as circumferentially adjacent ones of the columns 62. The columns 62 and recesses 60 can define circumferential centerlines that extend along planes that intersect the central hole axis 45. The circumferential centerlines of the columns can be circumferentially offset from circumferential centerlines of the recesses 60 by 45 degrees. Each of the columns 62 includes a plurality of thread segments 64. The thread segments 64 can be defined by the least one thread 46 that is divided into the thread segments 64 by the recesses 60. Thus, circumferentially adjacent ones of the columns 62 of thread segments are separated from each other by a respective one of the recesses 60. The thread segments 64 of each of the columns 62 can be discontinuous with respect to the thread segments 64 of the other ones of the columns 62 at the recesses 60. Thus, each of the recesses 60 interrupts the at least one thread 46 and divides the at least one thread 46 into the corresponding plurality of thread segments 64.

The thread segments 64 of each of the columns 62 can thus be circumferentially offset from the thread segments 64 of the other ones of the columns 62. Further, adjacent ones of the circumferentially spaced thread segments 64 can be separated by a common one of the recesses 60. Thus at least one or more of the thread segments 64 up to all of the thread segments 64 are aligned with at least one other of the thread segments 64 of an adjacent one of the columns 62 along the thread path. For instance, at least one or more of the thread segments 64 up to all of the thread segments 64 are aligned with at least one other of the thread segments 64 of an adjacent one of the columns 62 along a helical path. In one example, each of a plurality of the thread segments 64 of a respective one of the columns 62 is aligned along the thread path with 1) a first one the thread segments 64 of a first other one of the columns 62 that is adjacent the respective one of the columns 62 along a first circumferential direction, and 2) a second one the thread segments 64 of a second other one of the columns 62 that is adjacent the respective one of the columns 62 along a second circumferential direction that is opposite the first circumferential direction. Thus, the respective one of the columns 62 is disposed circumferentially between the first other one of the columns and the second other one of the columns. Further, the thread segments 64 of the respective one of the columns 62 is disposed between the first one of the thread segments 64 and the second one of the thread segments 64 with respect to the transverse direction T.

Each of the columns 62 can define a circumferential length in a respective plane oriented normal to the central hole axis 45. The circumferential length of each of the columns 62 can decrease in the radially inward direction. The thread segments 64 of each of the columns 62 are offset from each other along the transverse direction T. Further, each of the thread segments 64 defines first and second circumferentially opposed terminal ends. Each of the thread segments 64 defines a respective circumferential length from the first circumferentially terminal end to the second circumferentially terminal end. The circumferential lengths can be measured at the crests of the thread segments 64, which can be defined by the minor diameter. In one example, the circumferential lengths of the thread segments 64 decrease in the axially inward direction. In particular, the columns 62 define at least three consecutive ones of the thread segments 64 whose circumferential lengths decrease in the axially inward direction. It can thus also be said that the circumferential lengths of the at least three consecutive ones of the thread segments 64 increase in the axially outward direction. Thus, the axially outermost one of the thread segments 64 of each of the columns has a circumferential length greater than the axially innermost one of the thread segments 64 of each of the columns. The undercut 56 can be devoid of threads and smooth. Alternatively, the undercut 56 can define at least one thread segment 64 that is consecutive with an axially innermost one of the thread segments 64 of the each of the columns 62 along the thread path.

The circumferential lengths of the thread segments 64 of each of the columns 62 can decrease at a constant rate in the axially inward direction. Thus, the columns 62 of thread segments 64 can be conically tapered. Alternatively, the circumferential lengths of the thread segments 64 of each of the columns 62 can decrease at an increasing rate in the axially inward direction. Alternatively still, the circumferential lengths of the thread segments 64 of each of the columns 62 can decrease at a decreasing rate in the axially inward direction.

The columns 62 of thread segments 64 are each positioned so as to purchase with the threaded head 33 of the bone anchor 32 when the central anchor axis 53 of the bone anchor 32 is at an orientation with respect to the central hole axis 45 within a range of orientations at which the threaded head 33 is configured to mate with a plurality of the thread segments 64 of at least two of the columns 62. In one of the orientations within the range of orientations, the central anchor axis 53 can define an angle with the central hole axis 45 are within the range of angles in which the threaded head 33 is configured to threadedly mate with the at least one thread 46 in the fixation hole 38. In particular, the threaded head is configured to threadedly mate with at least a portion of at least two of the columns 62 when the bone anchor 32 is oriented such that the angle defined by the central anchor axis 53 and the hole axis 45 are within the range of angles. In one of the orientations within the range of orientations, the central anchor axis 53 can be coincident with the central hole axis 45.

The plate body 31, and thus the plate 30, can define at least one step 58 that project radially outward with respect to the internal surface 39 at the columns 62. For instance, the steps 58 can project radially outward from the internal surface 39 at the columns 62. The steps 58 can be oriented along a plane that is sloped with respect to a plane that is oriented normal to the central hole axis 45. For instance, each of the steps 58 can extend in the axially inward direction as it extends in the radially inward direction. Alternatively, the steps 58 can be oriented along a plane that is oriented normal to the central hole axis 45. Thus, it should be appreciated that the steps 58 can be oriented along any suitable direction as desired.

The steps 58 can separate the internal surface 39 at the columns 62 from the second region 49. The recesses 60 can separate circumferentially adjacent steps 58 from each other. Thus, the outer axial ends of the recessed surfaces 61 can extend circumferentially between adjacent steps 58. Alternatively, the recesses 60 can terminate axially inward of the steps 58, such that the steps 58 extend circumferentially continuously between the second region 49 and both the columns 62 and the recessed surfaces 61. Further, the outer surface 36 at the perimeter of the opening 29 can be defined by the second region 49 of the internal surface 39.

As described above, the internal surface 39 can define the second region 49 that extends between the axially outer surface 36 and both the columns 62 and the recessed surfaces 61. In one example, the second region 49 can extend from the axially outer surface 36 to the columns 62 and the recessed surfaces 61. Thus, locations of the second region 49 can be inline with respective ones of the columns 62 with respect to the transverse direction along respective planes that include the central hole axis 45, and other locations of the second region 49 can be inline with respective ones of the recessed surfaces 61 along respective planes that include the central hole axis 45. Thus, the axially outer end 54 of the inner surface 39 can be defined by the second region 49. It should be appreciated that the internal surface 39 at the columns 62 can be offset in the radially inward direction from the second region 49. That is, the internal surface 39 at the columns 62 can be disposed between the second region 49 and the central hole axis 45 with respect to the radial direction. The second region 49 can be circumferentially continuous and uninterrupted along an entire revolution along a constant curvature about the central hole axis along a plane that is oriented perpendicular to the central hole axis.

The second region 49 can be tapered radially inwardly as it extends in the axially inward direction. For instance, the second region 49 can be tapered radially inwardly from the axially outer surface 36 to the step 58. In one example, the second region 49 can be curved as it extends in the inward direction. For instance, the second region 49 can be concave as it extends along both a plane that includes the central hole axis, and a plane that is oriented perpendicular with respect to the central hole axis. Thus, the second region 49 can be concave along both the circumferential direction and the axial direction with respect to a view from inside the fixation hole 38. For example, the second region 49 can be dish shaped. The curvature of the second region 49 can be greater as it extends in the axial direction than the curvature of the second region 49 as it extends in the circumferential direction. The curvature of the second region 49 in the circumferential direction can be constant. Alternatively or additionally, the curvature of the second region 49 in the axial direction can be constant. In one example, the second region 49 can be spherical as it extends radially inwardly from its outer axial end to its inner axial end. The second region 49 can be unthreaded and smooth along its entirety. Alternatively, it is recognized that the second region 49 can define various textures as desired that are configured to abut the head of a compression screw in the manner described above. Thus, it can be said that the second region 49 can be devoid of threads configured to purchase with a threaded screw head.

The axially outer ends of the columns 62 can extend to the step 58. The steps 58 can be disposed between adjacent ones of the recesses 60 with respect to the circumferential direction. Thus, the steps 58 can be aligned with the columns 62 with respect to the transverse direction T. Thus, the columns 62 can extend from the step 58 to the axially inner surface 34. Alternatively, the columns 62 can extend from the step 58 to the undercut 56. Further, each of the steps 58 can be circumferentially tapered inwardly as it extends radially inwardly from a radially outer end to a radially inner end. The steps 58 can adjoin to the second 49 region at the radially outer end.

Further, at least a portion up to all of the internal surface 39 at each of the columns 62 can be tapered radially inwardly along its length as it extends in the axially inward direction. For instance, the internal surface 39 defines a respective region 63 that is tapered from its axially outer end to the undercut 56, or alternatively to the axially inner surface 34 of the undercut 56 is not present. The region 63 can be referred to as tapered threaded regions. The tapered threaded region 63 can include the plurality of columns 62 in the manner described above. The tapered threaded region 63 can be conical or alternatively shaped as desired. The tapered threaded region 63 can define an axially outer end and an axially inner end. The axially outer end of the tapered threaded region 63 can terminate at respective ones of the steps 58.

The second region 49 can extend between the outer surface 36 and both the steps 58 and the recessed surfaces 61. That is, the second region 49 can be bound at its axially inner end by the steps 58 and the recessed surfaces 61. The second region can be bound at its axially outer end by the outer surface 36. Alternatively, if the bone plate 30 does not include the steps 58, the second region 49 can extend between the outer surface 36 and both the steps 58 and the recessed surfaces 61. That is, the second region 49 can be bound at its axially inner end by the steps 58 and the recessed surfaces 61 the second region 49 can be bound at its axially inner end by the columns 62 and the recessed surfaces 61. Thus, if the bone plate 30 does not include the steps 58, the axially outer end of the tapered threaded region 63 can terminate at their respective axially outer ends at the second region 49. Thus, the second region 49 can extend axially outward from the second region 49.

Alternatively still, if the bone plate 30 does not include the second region 49 as illustrated in FIGS. 9A-9B, then the axially outer end of the tapered threaded region 63 can terminate at the axially outer surface 36. The axially inner end of the tapered threaded region 63 can be defined at the undercut 56. Alternatively, if the bone plate does not include the undercut 56, then the axially inner end of the tapered threaded region 63 can be defined by the axially inner surface 34. The circumferential lengths of consecutive thread segments 64 of each of the columns 62 can increase in the axially inward direction. The consecutive thread segments can be defined by the tapered threaded region 63.

The internal surface 39 at the radially innermost edge of the step 58 can define a constant curvature along its circumferential length along a plane that is oriented normal to the central hole axis 45. The constant curvature can, for instance, extend along a circular path. The recessed surfaces 61 can similarly define a constant circumferential curvature along the same plane that is oriented normal to the central hole axis 45. The circumferential curvature of the recessed surfaces 61 can be greater than the circumferential curvature of the step 58. Thus, the circumferential curvature of the step 58 can be defined by a first radius, and the circumferential curvature of the recessed surface 61 can be defined by a second radius that is less than the first radius. The step 58 can be defined by a radially outermost edge opposite the radially innermost edge. The radially outermost edge of the step can have a total circumferential length of between 6 mm and 10 mm, for instance between approximately 7 mm and approximately 9 mm, for instance approximately 8.8 mm.

The first and second ends of an entirety of the recessed surface 61 at each axial location the respective recess 60 can diverge away from each other as they adjoin the internal surface 39. Further, a straight line that extends from the first end of the recessed surface 61 to the second end of the recessed surface 61 at every axial location of the recesses 60 can define a chord of a circle that defines the circular path of the recessed surface 61. The chord can be disposed between the center of the circle and the recessed surface 61. Thus, the first and second ends of the recessed surface define a circumferential length that is less than or equal to (e.g, no more than) 180 degrees of the circle that defines the circular path of the recessed surface 61 along a plane that is normal to the central hole axis 45, along an entirety of each of the recesses 60. For instance, the straight line can alternatively define the diameter of the circle. The circumferential length of the recessed surface 61 can decrease along the axially outward direction. For instance, the recessed surface 61 can define a minor arc along the plane from the first end of the recessed surface 61 to the second end of the recessed surface 61, along an entirety each of the recesses 60. The recessed surface 61 defines a curvature in the circumferential direction that is greater than the curvature of the internal surface 39 at the columns 62 along a common plane that is oriented perpendicular to the central hole axis 45.

The recesses 60 can be oriented in any direction as desired. For instance, the recessed surfaces 61 can each be radially outwardly sloped with respect to the central hole axis 45 as it extends along the axially outward direction. Alternatively, the recessed surfaces 61 can be spaced from the central hole axis 45 a constant distance along an entirety of their axial length along a plane that includes the central hole axis 45. Further, the circumferential length of the recessed surface 61 can increase as the recessed surface 61 extends in the axially inward direction along a respective plane that 1) is oriented normal to the central hole axis 45 and 2) is disposed at a location whereby it further extends into the columns 62.

The undercut 56 can extend radially out from the axially inner end of the tapered threaded region 63 of the internal surface 39. Further, the undercut 56 can carry a portion of the at least one thread 46, and thus can define a portion of the columns 62. Alternatively, the undercut 56 can be devoid of threads. In one example, one or both of the step 58 and the second region 49 of the internal surface 39 can be devoid of threads that are designed to purchase with the threaded head 33 of the bone anchor 32. Thus, one or both of the step 58 and the second region 49 of the internal surface 39 can be said to be substantially smooth.

The internal surface 39 at each of the columns 62 from the axially outer end of the column to the axially inner end of the column 62 can define any suitable surface area as desired. For instance, the columns 62 can cumulatively define a surface area that is between approximately 3 mm$^2$ and approximately 6 mm$^2$, such as between approximately 4 mm$^2$ and approximately 5 mm$^2$, and in one example can be approximately 4.2 mm$^2$. The axially outer edge of at least one of the columns, up to all of the columns 62, can have a first circumferential length, and the axially inner edge of at least one of the columns, up to all of the columns 62, can have a second circumferential length that is between approximately 45% and approximately 90% of the first circumferential length. For instance, the second circumferential length can be between approximately 60% and approximately 80% of the first circumferential length. In one example, the second circumferential length can be between approximately 75% and 80% of the first circumferential length. For example, the first circumferential length can be approximately 77% of the first circumferential length. The first circumferential length can be between approximately 0.75 mm and approximately 2.5 mm, such as between approximately 1 mm and approximately 2 mm, for instance approximately 1.5 mm. The second circumferential length can be between approximately 0.5 mm and approximately 2 mm, such as between approximately 0.75 mm and approximately 1.5 mm, for instance approximately 1.2 mm.

Fabrication of the bone plate 30 can include the step of creating a through-hole through the bone plate body 31 from the axially outer surface 36 to the axially inner surface 34. The creating step can, for instance, include the step of creating the through-hole through the bone plate body 31 so as to define an interior surface of the bone plate body 31. The through-hole can be created such that the interior surface of the bone plate body tapers radially inward toward the central hole axis 45 as it extends in the axially inward direction, as described above. The creating step can, in one example, include the step of drilling the through-hole through the bone plate body 31. The drilling step can be performed in a single step, or in multiple steps of creating a through-hole, and then defining the through-hole to have a conical shape. Further, the drilling step can include the step of creating a counterbore so as to define the step 58 and the corresponding second region 49 as described above. However, as recognized from the description below, the bone plate 30 can be devoid of the step 58, such that the internal surface 39 defines the columns 62 and not the second region 49. Thus, the step of creating a counterbore can define the second region 49 without defining the step 58. Accordingly, the internal surface 39 can define a constant taper from the axially outer surface 36 to the undercut 56, or to the axially inner surface 34 if the bone plate 30 does not include the undercut. The method can further include the step of creating the undercut 56 at the axially inner surface 34. The undercut 56 can be created during the step of creating the through-hole, or after the through-hole has been created.

Next, the method can include the step of cutting the at least one thread 46 into the interior surface so as to define the internal surface 39 and the at least one thread 46. It should be appreciated that the minor diameter of the at least one thread 46 can be defined by the crest of the at least one thread, and the major diameter of the at least one thread can be defined by the internal surface 39. The at least one thread 46 can define a height from the minor diameter to the major diameter along its length. In one example, the height can be constant along at least a plurality of revolutions of the at least one thread 46 about the central hole axis 45. Thus, the minor diameter of the thread can lie on a conical geometric shape. In another example, the height can increase or decrease along the length of the at least one thread 46 as the at least one thread 46 extends in the axially inward direction. The method can include the step of creating the recesses 60 in the internal surface 39. The step of creating the recesses 60 can similarly create the columns 62. Thus, the step of creating the recesses 60 can be performed after the at least one thread is formed 46. Alternatively, the step of creating the recesses 60 can be performed prior to forming the at least one thread 46. The recesses 60 can be created in the interior surface to define the columns 62, and the at least one thread 46 can then be created in the columns 62 so as to define the interior surface 39 and the at least one thread. Because the recessed surfaces 61 are curved along an entirety of their length along a plane oriented normal to the central hole axis 45, the step of creating the recesses 60 can be achieved by drilling into the bone plate 30 along at least a portion of the internal surface 39 or the interior surface. Thus, each of the recesses 60 defines a circumferential end that is open at the internal surface 39. In one example, each of the recesses 60 can be drilled into the axially inner surface 34 along the axially inward direction, such that the inner end of the recesses 60 have a radial depth that increases as the recesses 60 extend in the axially outward direction. The radial depth of the recesses 60 can be selected so as to define the columns 62 of thread segments 64 as described above.

The bone plate body 31 can define a height along the transverse direction T from the axially inner surface 34 to the axially outer surface 36. The bone plate body 31 can define a height from the axially outer edge of the undercut 56 to the second region between approximately 0.9 mm and approximately 3.0 mm, such as approximately 2.25 mm. The bone plate body 31 can have a height from the axially inner surface 34 to the axially outer end of the columns 62 (and thus the tapered threaded region 63) of between approximately 0.75 mm and approximately 2 mm, such as between approximately 1 mm and approximately 1.5 mm, such as approximately 1.3 mm. The height of each of the columns 62 can be from the axially outer edge of the undercut 56 (or the axially inner surface 34 if the undercut 56 is not included) and the axially outer edge of the columns 62 of between approximately 0.7 mm and approximately 1.3 mm, such as approximately 1.2 mm.

Figure 7:
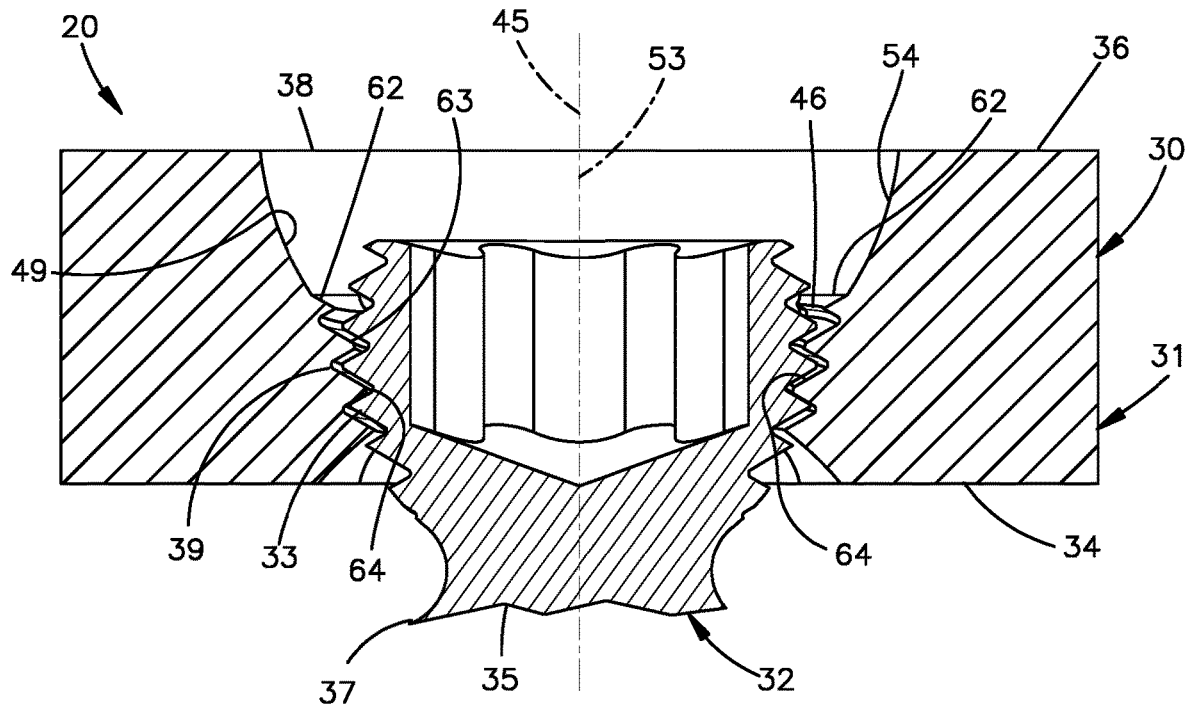
FIG. 7 is a sectional side elevation view of the portion of the bone plate illustrated in FIG. 3A, shown with a bone anchor threadedly mated to the bone plate inside the variable angle locking hole at a first orientation.
Figure 8:
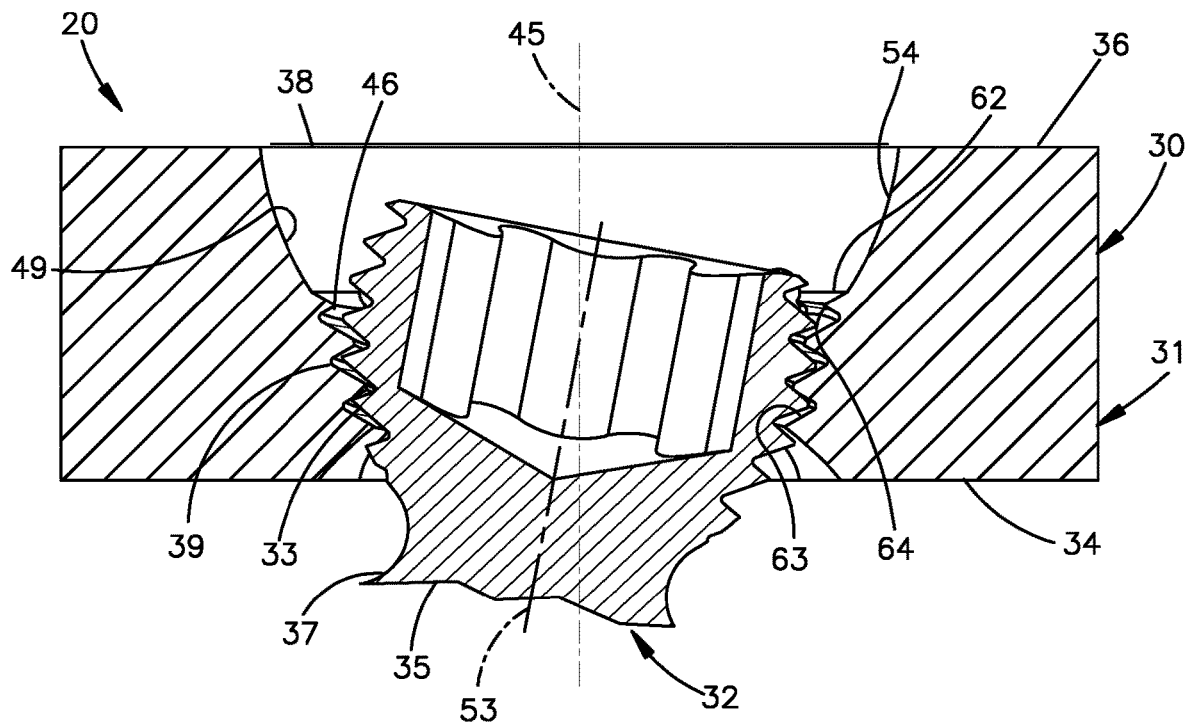
FIG. 8 is a sectional side elevation view of the portion of the bone plate illustrated in FIG. 7, shown with a bone anchor threadedly mated to the bone plate inside the variable angle locking hole at a second orientation different than the first orientation.

A method of bone fixation using the bone fixation system 20 will now be described with further reference to FIGS. 7-8. In particular, the bone plate 30 is brought into proximity with the underlying bone. For instance, the axially inner surface 34 can be brought into contact with the underlying bone, or can be spaced from the underlying bone. A plurality of bone anchors can be inserted through respective bone fixation holes 38 of the bone plate 30 so as to fix the bone plate 30 to the underlying bone at opposite locations of a bone defect of the underlying bone. The method of fixing the bone plate 30 to the underlying bone through the variable angle locking holes 44 includes the step of inserting the shaft 35 of the bone anchor 32 through the fixation hole 38, which can be configured as the variable angle locking hole 44, and into the underlying bone. The bone anchor 32 can be rotated about the central anchor axis 53 so as to drive the shaft 35 into the underlying bone. As the bone anchor 32 is being driven into the bone, the central anchor axis 53 can define any suitable angle with respect to the central hole axis 45 within a range of angles. The range of angles can extend from 0 degrees to 15 degrees as defined by the central anchor axis 53 and the central hole axis 45 in any direction about the central hole axis 45, that is along the full 360 degree circumference about the central hole axis 45. The range of angles can be achieved when bone screw fixation instrumentation, such as a drill guide, is also inserted into the fixation hole 38. The range of angles of the central hole axis 45 with respect to the central anchor axis 53 can define a cone about the central hole axis 45. Thus, the central hole axis 45 can define the axis of the cone.

Continuing rotation of the bone anchor 32 while the angle defined by the central anchor axis 53 and the central hole axis 45 is in the range of angles causes the threaded head 33 to advance into the variable angle locking hole 44, such that the threaded head 33 threadedly mates with the at least one thread 46 of the variable angle locking hole 44. For instance, a portion of the threaded head 33 can threadedly mate with the at least one thread at a plurality, e.g., at least two, of the columns 62. It is recognized that different angles between the central anchor axis 53 and the central hole axis 45 will cause the threaded head 33 to threadedly purchase with different locations of the at least one thread 46 with respect to the transverse direction T.

A compression screw can be inserted through a second one of the fixation holes 38, until 1) the shaft of the compression screw is threadedly driven into underlying bone, and 2) the head of the compression screw bears against the second region 49 to apply a compression force against the bone plate toward the underlying bone.

Without being bound by theory, it is believed that the recesses 60 assist in the ability of the bone anchor 32 to angulate with respect to the central hole axis 45 within the range of angles while threadedly purchasing with the at least one thread 46. Further, without being bound by theory, it is believed that the ability of the threaded head 33 to threadedly purchase with the columns 62 of thread segments 64 can provide more reliable fixation than conventional variable angle locking holes.

Referring now to FIGS. 9A-9B, it is recognized that the plate 30 can be constructed in accordance with numerous examples, some of which have been described above. In one example, the bone plate 30 can be devoid of the step 58 and the second region 49 of the internal surface 39. Accordingly, the surface that previously defined the step 58 of the bone plate 30 can define the axially outer surface 36. Thus, each of the columns 62, can extend from the axially outer surface 36 to the undercut 56. Alternatively, the at least one thread 46 can extend to the undercut 56, such that the columns 62 extend from the axially outer surface 36 to the axially inner surface 34. Alternatively, the bone plate can be devoid of the undercut 56, such that the columns 62 extend from the axially outer surface 36 to the axially inner surface 34.

Without being bound by theory, it is believed that removing the second region 49 allows the bone plate 30 to have a decreased height with respect to conventional variable angle bone plates while exhibiting reliable purchase between the threaded screw head 33 and the bone plate 30 in the variable angle locking hole 44. Thus, in one example, the height of the bone plate 30 from the axially inner surface 34 to the axially outer surface 36 along the transverse direction T can be between approximately 0.75 mm and approximately 2 mm, such as between approximately 1 mm and approximately 1.5 mm, such as approximately 1.3 mm.

The embodiments described in connection with the illustrated embodiments have been presented by way of illustration, and the present invention is therefore not intended to be limited to the disclosed embodiments. Accordingly, those skilled in the art will realize that the invention is intended to encompass all modifications and alternative arrangements included within the spirit and scope of the invention, as set forth by the appended claims.

What is claimed:

1. A bone plate comprising:
   an inner surface configured to face bone, and an outer surface opposite the inner surface;
   an internal surface that extends from the outer surface to the inner surface, the internal surface defining a fixation hole that extends from the outer surface to the inner surface along a central hole axis and is sized to receive a shaft of a bone anchor that is 1) a variable angle locking screw having a threaded head, or 2) a compression screw having an unthreaded head, wherein the shaft of the bone anchor extends along a central anchor axis;
   wherein the internal surface defines 1) a tapered threaded region that includes a plurality of threaded columns that are circumferentially spaced from each other about the central hole axis and separated from each other by a corresponding plurality of recesses, and 2) a second region that extends between an outer end of the tapered threaded region and the outer surface, the second region being concave as it extends along both a plane that includes the central hole axis, and a plane that is oriented perpendicular with respect to the central hole axis,
   wherein 1) the tapered threaded region is configured to threadedly mate with the threaded head of the variable angle locking screw while the central anchor axis is oriented at a first orientation with respect to the central hole axis, 2) the tapered threaded region is further configured to threadedly mate with the threaded head of the variable angle locking screw while the central anchor axis is oriented at a second orientation with respect to the central hole axis that is different than the first orientation, and 3) the second region is configured to receive a compression force from the unthreaded head of the compression screw that is inserted into the fixation hole such that a head of the compression screw abuts the second region, and
   wherein the second region has a curvature as it extends along a direction from the outer surface to the inner surface that is greater than a curvature of the second region in a circumferential direction about the central hole axis.

2. The bone plate as recited in claim 1, wherein first locations of the second region are aligned with respective ones of the columns along respective planes that include the central hole axis, and second locations of the second region are inline with respective ones of the recesses along respective planes that include the central hole axis.

3. The bone plate as recited in claim 1, wherein the internal surface at the columns is offset toward the central hole axis with respect to the internal surface at the second region.

4. The bone plate as recited in claim 1, wherein the second region has a constant curvature about the central hole axis along a plane that is oriented perpendicular to the central hole axis.

5. The bone plate as recited in claim 4, wherein the second region is circumferentially continuous and uninterrupted along an entire revolution about the central hole axis along the plane that is oriented perpendicular to the central hole axis.

6. The bone plate as recited in claim 1, wherein the second region is tapered toward the central hole axis as it extends in a direction from the outer surface toward the inner surface.

7. The bone plate as recited in claim 1, wherein the second region has a substantially constant curvature as it extends circumferentially about the central hole axis.

8. The bone plate as recited in claim 1, wherein the second region is devoid of threads configured to purchase with a threaded screw head.

9. The bone plate as recited in claim 1, wherein the inner surface further defines a step that extends radially outward from the tapered threaded region to the second region.

10. The bone plate as recited in claim 1, wherein at least one of the columns defines an axially outer edge that has a first circumferential length about the central hole axis, and an axially inner edge that has a second circumferential length about the central hole axis that is between approximately 45% and approximately 90% of the first circumferential length.

* * * * *